(12) United States Patent
Jackson et al.

(10) Patent No.: US 11,803,243 B2
(45) Date of Patent: Oct. 31, 2023

(54) ELECTRONIC DEVICE HAVING A HAPTIC DEVICE WITH AN ACTUATION MEMBER AND A RESTORATION MECHANISM

(71) Applicant: Apple Inc., Cupertino, CA (US)

(72) Inventors: Benjamin G. Jackson, Redwood City, CA (US); Brenton A. Baugh, Los Altos Hills, CA (US); Megan A. McClain, San Francisco, CA (US); Steven J. Taylor, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/857,922

(22) Filed: Jul. 5, 2022

(65) Prior Publication Data

US 2022/0350411 A1 Nov. 3, 2022

Related U.S. Application Data

(63) Continuation of application No. 16/820,450, filed on Mar. 16, 2020, now abandoned.

(60) Provisional application No. 62/832,860, filed on Apr. 11, 2019.

(51) Int. Cl.
*G06F 3/01* (2006.01)
*G06F 3/0488* (2022.01)
*G06F 3/044* (2006.01)

(52) U.S. Cl.
CPC .............. *G06F 3/016* (2013.01); *G06F 3/015* (2013.01); *G06F 3/0447* (2019.05); *G06F 3/0488* (2013.01); *G06F 2203/04106* (2013.01)

(58) Field of Classification Search
CPC ........ G06F 3/0488; G06F 3/015; G06F 3/016; G06F 3/0447; G06F 2203/011; G06F 2203/04106; G04G 17/04; G04G 13/023; G04G 21/08; A61B 5/332; A61B 5/7455; A61B 5/681; G04C 21/02; G04C 21/08
USPC ................................................. 345/173, 156
See application file for complete search history.

(56) References Cited

U.S. PATENT DOCUMENTS

| 8,051,656 | B1 | 11/2011 | Cripe et al. |
| 8,584,456 | B1 | 11/2013 | McKnight |
| 2009/0302708 | A1 | 12/2009 | Takahashi |
| 2016/0058375 | A1 | 3/2016 | Rothkopf |
| 2016/0255944 | A1 | 9/2016 | Baranski |
| 2019/0004603 | A1 | 1/2019 | Longo |
| 2019/0101986 | A1* | 4/2019 | Khoshkava ........... H01L 41/193 |
| 2019/0124189 | A1* | 4/2019 | Grant ...................... G06F 3/016 |
| 2020/0326779 | A1 | 10/2020 | Jackson et al. |

\* cited by examiner

*Primary Examiner* — Jimmy H Nguyen
(74) *Attorney, Agent, or Firm* — Brownstein Hyatt Farber Schreck, LLP

(57) ABSTRACT

A haptic device for an electronic device includes an actuation member formed from a shape-memory alloy (SMA) material that changes shape (e.g., expands or contracts) in response to an applied electrical current. In some cases, the haptic devices described herein also include a restoration mechanism that restores the actuation member to its original shape or to a similar shape. The change in the shape of the actuation member and the restoration of the shape of the actuation member may produce a haptic output at the electronic device.

20 Claims, 31 Drawing Sheets

ELECTRONIC DEVICE HAVING A HAPTIC DEVICE WITH AN ACTUATION MEMBER AND A RESTORATION MECHANISM

CROSS-REFERENCE TO RELATED APPLICATIONS

This application is a continuation of U.S. patent application Ser. No. 16/820,450, filed Mar. 16, 2020, which is a non-provisional application and claims the benefit of U.S. Provisional Patent Application No. 62/832,860, filed Apr. 11, 2019, the disclosures of which are hereby incorporated by reference herein in their entirety.

FIELD

The described embodiments relate generally to an electronic watch or other electronic device. More particularly, the described embodiments relate to providing haptic feedback using an actuation member formed from a shape-memory alloy.

BACKGROUND

Modern day electronic devices have a broad range of functionality and have become more portable and compact. Some portable electronic devices may be adapted to receive user input and, in response, provide an output or other response. Some portable electronic devices include a speaker or other type of output device that is adapted to provide an output to a user. However, some traditional output devices are bulky and may not be optimized for various user feedback scenarios. The systems and techniques described herein may be used to provide a compact output device for a portable electronic device that may provide advantages over some traditional systems.

SUMMARY

Embodiments of the systems, devices, methods, and apparatuses described in the present disclosure are directed to an electronic watch or other electronic device having a haptic device with an actuation member formed from a shape-memory alloy and a restoration mechanism, and methods for providing haptic outputs using the haptic device.

The embodiments described herein include an electronic watch having an enclosure, a touch-sensitive display, a processing unit, and a haptic device. The touch-sensitive display may be positioned at least partially within the enclosure. The processing unit may be operably coupled to the touch-sensitive display. The haptic device may be positioned at least partially within the enclosure and configured to provide a haptic output along an external surface of the enclosure. The haptic device may include an actuation member formed from a shape-memory alloy material and configured to contract in response to a signal generated by the processing unit and produce at least a portion of the haptic output. The haptic device may further include a restoration mechanism coupled to the actuation member and configured to elongate the actuation member after a contraction of the actuation member.

In some embodiments, the actuation member is a first actuation member formed from a first shape-memory alloy material and the signal is a first signal. The restoration mechanism may include a second actuation member formed from a second shape-memory alloy material. The second actuation member may be configured to contract in response to a second signal generated by the processing unit.

In some cases, the enclosure includes a cover defining at least a part of a front external surface of the enclosure and a contact member defining at least a part of a rear external surface of the enclosure. A graphical output of the touch-sensitive display may be visible along the front external surface. The rear external surface may be configured to contact a body part of a user. The haptic device may be configured to produce the haptic output along the rear external surface by moving the contact member relative to the cover. In some cases, the haptic output may be coordinated with a change in the graphical output. In some cases, the haptic device is configured to rotate the contact member. In some cases, the haptic device is configured to translate the contact member along either a path that is parallel to the front external surface or a path that is perpendicular to the front external surface.

In some cases, the electronic watch additionally includes a crown that is configured to receive a rotational input, and the haptic output is provided in response to the rotational input. In some cases, the actuation member is configured to produce a first portion of the haptic output and the restoration mechanism is configured to produce a second portion of the haptic output. In some cases, the signal is a first signal, and the processing unit is further configured to produce a second signal after the restoration mechanism elongates the actuation member, and the actuation member is configured to produce a third portion of the haptic output in response to the second signal.

The embodiments described herein further include an electronic watch having an enclosure, a display, an actuation member, a restoration mechanism, and a processing unit. The display may be positioned at least partially within the enclosure. The actuation member may comprise a shape-memory alloy and may be positioned within the enclosure. The actuation member may be configured to change from a first shape to a second shape in response to an electrical current or electrical signal. The restoration mechanism may be coupled to the actuation member and may be configured to restore the actuation member from the second shape to the first shape. The processing unit may be operably coupled to the actuation member and configured to cause the electrical current or electrical signal to be applied to the actuation member. Changing the actuation member from the first shape to the second shape may produce a first portion of a haptic output along an external surface of the enclosure. Restoring the actuation member from the second shape to the first shape may produce a second portion of the haptic output along the external surface of the enclosure.

In some cases, the enclosure includes a cover positioned over the display, a housing member defining an opening, and a rear cover positioned in the opening and coupled to the actuation member. The actuation member may cause the rear cover to move relative to at least one of the cover or the housing member to produce the haptic output. In some cases, changing the actuation member from the first shape to the second shape causes the rear cover to move in a first direction and restoring the actuation member from the second shape to the first shape causes the rear cover to move in a second direction that is opposite to the first direction. In some cases, the actuation member causes the rear cover to rotate relative to at least one of the cover or the housing member. In some cases, the rear cover includes an electrode for determining an electrocardiogram and the haptic output is provided in response to determining the electrocardiogram.

In some cases, the actuation member is a first actuation member, and the restoration mechanism includes a second actuation member. In some cases, the restoration mechanism includes a spring.

The embodiments described herein further include a method for producing a haptic output using an actuation member comprising a shape-memory alloy. The method includes the steps of detecting an input at the electronic device, and in response to the input, determining, by a processing unit of the electronic device, an output to be produced by the electronic device. The method further includes the steps of outputting, by the processing unit, an output signal to provide a haptic output that corresponds to the determined output and, in response to the output signal, applying an electrical current or electrical signal to an actuation member of the electronic device to contract the actuation member. The method further includes the step of elongating the actuation member using a restoration mechanism of the electronic device. Contracting the actuation member produces a first portion of the haptic output and elongating the actuation member produces a second portion of the haptic output.

In some cases, the electrical current is a first electrical current and the method further includes contracting the actuation member after the actuation member is elongated by applying a second electrical current to the actuation member to produce a third portion of the haptic output.

In some cases, the method further includes displaying a graphical output using a touch-sensitive display and detecting the input comprises detecting a touch input along the touch-sensitive display.

In some cases, detecting the input includes determining an electrocardiogram using one or more voltages detected at the electronic device, and the haptic output is provided in response to determining the electrocardiogram.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1:
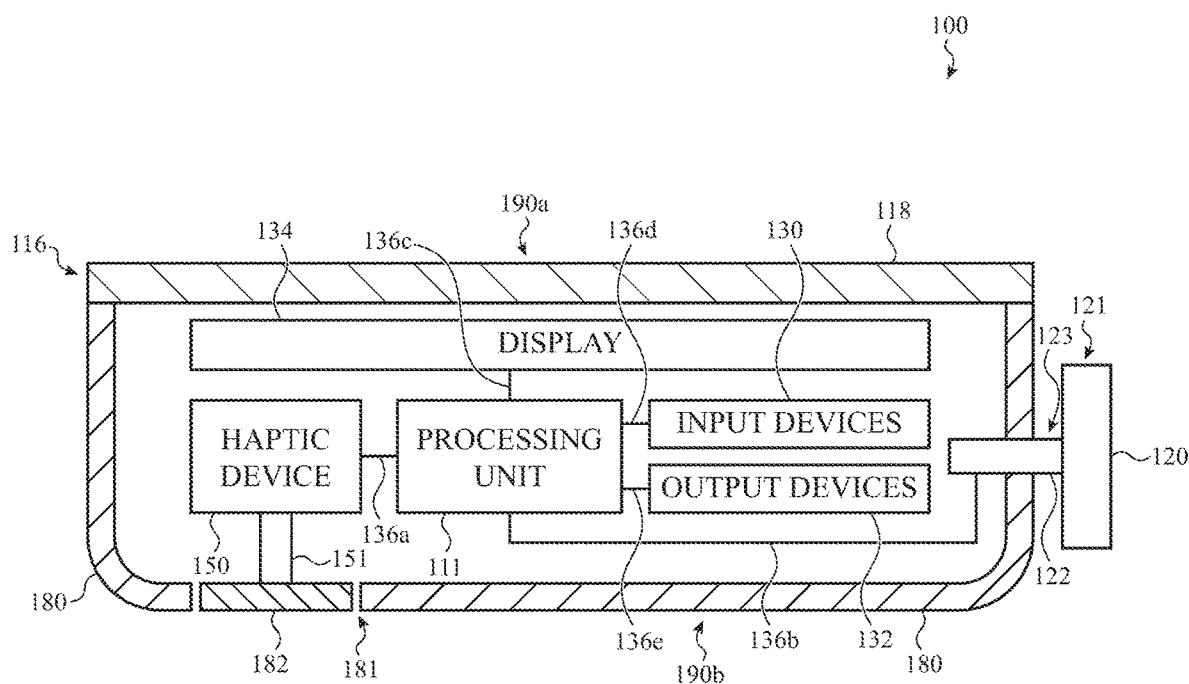
FIG. 1 shows a functional block diagram of an example electronic device that incorporates a haptic device with an SMA actuation member and a restoration mechanism.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to an electronic device (e.g., an electronic watch) having a haptic device for providing haptic outputs to a user of the device. In various embodiments, the haptic device includes an actuation member formed at least partially from a shape-memory alloy (SMA) material that changes shape (e.g., expands or contracts) in response to an applied electrical current or electrical signal. The actuation member (referred to herein as an "SMA actuation member") may produce a haptic output along a surface of the electronic device. In some cases, the haptic devices described herein also include a restoration mechanism that restores the SMA actuation member to its original shape or to a similar shape. The change in the shape of the SMA actuation member and the restoration of the shape of the SMA actuation member may combine to produce a haptic output at the electronic device.

As noted above, an SMA actuation member may contract from a first shape to a second shape in response to an applied electrical current or electrical signal. Once the electrical current ceases or is reduced below a threshold, the SMA actuation member may elongate (e.g., expand) from the second shape to the first shape or to a shape between the first and second shapes. In some cases, the SMA actuation member may be successively or repeatedly contracted several times to produce multiple portions of a haptic output. In many cases, the time required for elongation of the SMA actuation member is sufficiently long that it limits the number of successive contractions and elongations that can occur in a given time period.

The restoration mechanisms described herein may apply a tensile force to an SMA actuation member to increase the speed of elongation and reduce the time required for elongation. As a result, an SMA actuation member may be contracted and elongated more frequently, and can provide more haptic outputs or portions of haptic outputs in a given time period.

As used herein, the terms "haptic output" and "tactile output" may be used to refer to outputs produced by the electronic device that may be perceived through user touch. Examples of haptic outputs include vibrations, deflections, and other movements of a device enclosure, a device cover, and input device, or another device component that forms a portion of the external surface of the electronic device. In some cases, a haptic device may vibrate and/or deflect a device component (e.g., an enclosure, a cover, or an input device) to produce a haptic output at a portion of the external surface of the device defined by the device component. In some cases, haptic outputs may be produced by relative movement of one or more device components with respect to one or more additional device components. As one example, a haptic device may cause a first device component (e.g., a cover) to vibrate, oscillate, rotate, and/or translate relative to another device component (e.g., an enclosure) to produce a haptic output that may be perceived by a user.

In some cases, the haptic device is coupled to an enclosure of the electronic device, and the haptic device provides haptic outputs that may be tactilely perceived by the user along one or more portions of an external surface of the electronic device. In some cases, the haptic device is coupled to a contact member that moves (e.g., oscillates, vibrates, translates, or rotates) with respect to other components of the electronic device, such as a housing member, to provide haptic outputs. Translation may include inward and outward translation, lateral translation, and other movement of the contact member. In some cases, the haptic device provides haptic outputs by deflecting a portion of an enclosure of the electronic device. Different types of movement may be used to provide different haptic outputs.

In some cases, the haptic outputs described herein are localized haptic outputs. As used herein, the term "localized haptic output" may be used to refer to a haptic output that is primarily perceived along a particular location or region of the external surface of the electronic device. The particular location or region may correspond to a portion of the exterior of the electronic device that is likely to be contacted by the user and thereby more readily perceived without producing the output along an entirety of the exterior of the electronic device. The haptic devices described herein may produce localized haptic outputs causing vibration, deflection, or movement at particular locations or regions of the external surface of the electronic device. In some cases, a localized haptic output may be felt strongly at one or more locations or regions of the external surface and may be imperceptible or less perceptible at one or more other locations or regions of the external surface of the electronic device.

As suggested above, a localized haptic output may be provided at one or more locations that are configured to be contacted by a user. For example, localized haptic outputs may be provided at a rear surface of an electronic watch that is configured to contact a user's wrist while the watch is worn. In some cases, localized haptic outputs may provide feedback regarding inputs received at particular locations of the electronic device. For example, localized haptic outputs may be provided at and/or near an input device (e.g., a button, a crown, or a touchscreen) to provide feedback related to an input provided at the input device. In other cases, localized haptic outputs may provide other types of feedback or information to users.

In some cases, the haptic outputs described herein are global haptic outputs. As used herein, the term "global haptic output" may be used to refer to a haptic output that is caused by a moving mass or other inertial effect. As described herein, a haptic device may cause a mass or weighted member to move and, in some cases, oscillate, to produce a perceptible vibration or tactile effect along an external surface of the electronic device. In general, a global haptic output may be produced over a large area and, in some cases, substantially all of the external surfaces or a substantial entirety of an exterior of the electronic device. In general, global haptic outputs are not meant to be localized to any particular location or region of the external surface of the electronic device. In some cases, global haptic outputs may provide feedback that is not related to a specific location on the electronic device. For example, global haptic outputs may be provided for alerts received at the electronic device. In other cases, global haptic outputs may provide other types of feedback or information to users.

The term "attached," as used herein, may be used to refer to two or more elements, structures, objects, components, parts or the like that are physically affixed, fastened, and/or retained to one another. The term "coupled," as used herein, may be used to refer to two or more elements, structures, objects, components, parts, or the like that are physically attached to one another, operate with one another, communicate with one another, are in electrical connection with one another, and/or otherwise interact with one another. Accordingly, while elements attached to one another are coupled to one another, the reverse is not required. As used herein, "operably coupled" or "electrically coupled" may be used to refer to two or more devices that are coupled in any suitable manner for operation and/or communication, including wired, wirelessly, or some combination thereof.

As noted above, the actuation members described herein may be formed at least partially from one or more shape-memory alloy (SMA) materials that change shape (e.g., expands or contracts) in response to an applied electrical current. Examples of SMA materials include copper alloys (e.g., copper-aluminum-nickel), nickel alloys (e.g., nickel-titanium), zinc alloys (e.g., copper-zinc-aluminum), cobalt alloys (e.g., cobalt-nickel-gallium alloys), silver alloys (e.g., silver-cadmium), titanium alloys (e.g., titanium-niobium), gold alloys (e.g., gold-cadmium), iron alloys, and other alloy materials.

These and other embodiments are discussed with reference to FIGS. 1-12. However, those skilled in the art will readily appreciate that the detailed description given herein with respect to these figures is for explanatory purposes only and should not be construed as limiting.

FIG. 1 shows a functional block diagram of an example electronic device 100 that incorporates a haptic device 150 with an SMA actuation member and a restoration mechanism. In some examples, the device 100 may be an electronic watch. The electronic device 100 may include a device enclosure 116, a haptic device 150, a crown 121, one or more input devices 130, one or more output devices 132, a display 134, and a processing unit 111 positioned at least partially within the enclosure 116.

In some cases, the electronic device 100 includes a haptic device 150 positioned at least partially within the enclosure 116 and configured to provide haptic outputs along an external surface of the electronic device 100. As noted above, the haptic device may include an actuation member formed from a shape-memory alloy that changes shape (e.g., expands or contracts) in response to an applied current or other electrical signal. The SMA actuation member may be configured to contract in response to a signal generated by the processing unit 111 and produce at least a portion of a haptic output. As described herein, the processing unit may produce an electrical signal that is used to trigger the generation of an electrical current or other electrical signal that drives the SMA actuation member. The SMA actuation member is not typically driven directly by the signal produced by the processing unit.

In some cases, the haptic device 150 also includes a restoration mechanism that restores (e.g., elongates) the SMA actuation member to its original shape or to a similar shape. The changes in the shape of the SMA actuation member (e.g., contraction and/or elongation) may combine to produce a haptic output at the electronic device 100. For example, the SMA actuation member may produce a first portion of a haptic output and the restoration mechanism may produce a second portion of a haptic output. As described herein, the restoration mechanism may include a spring, a mechanical restoring member, and/or another actuation member formed from the same or another SMA material.

The haptic device 150 may produce haptic outputs in response to receiving one or more signals from the processing unit 111. In some cases, the haptic outputs may correspond to inputs received by the electronic device 100 (e.g., a rotational input received by the crown 121) and/or outputs provided by the electronic device (e.g., a graphical output provided by the display 134). The haptic outputs may correspond to operational states, events, or other conditions at the electronic device 100, including inputs received at the electronic device (e.g., touch inputs, rotational inputs, translational inputs), outputs of the electronic device (e.g., graphical outputs, audio outputs, haptic outputs), applications and processes executing on the electronic device, predetermined sequences, user interface commands (e.g., volume, zoom, or brightness controls, audio or video controls, scrolling on a list or page, and the like), and the like. The haptic device 150 may be operably coupled to the processing unit 111 via a connector 136a and/or via one or more additional components of the electronic device 100.

In various embodiments, the haptic device 150 is coupled to the enclosure 116 to provide the haptic output along one or more external surfaces of the electronic device 100 defined by the enclosure 116 or other components of the electronic device 100. For example, the enclosure 116 may define a front external surface 190a and a rear external surface 190b of the device 100. In some cases, the SMA actuation member and/or the restoration mechanism of the haptic device 150 may be coupled to the enclosure 116 and may deflect or otherwise move one or more portions of the enclosure 116 to produce a haptic output.

In some cases, the enclosure 116 includes one or more separate components. For example, as shown in FIG. 1, the enclosure 116 may include a cover 118, a housing member 180, and a contact member 182. In some cases, the cover 118 defines at least part of the front external surface 190a, and the housing member 180 and the contact member 182 cooperate to define at least part of the rear external surface 190b. In some cases, the cover 118 is positioned at over and/or at least partially in an opening 110 defined by the housing member 180. In some cases, the contact member 182 is positioned in an opening 181 defined by the housing member 180.

In various embodiments, the haptic device 150 may provide local haptic outputs along the external surface of the electronic device 100 (e.g., one or more locations along the front external surface 190a, the rear external surface 190b, or elsewhere along the electronic device 100). In some cases, the haptic device 150 may provide global haptic outputs along the external surface of the electronic device.

In some cases, the haptic device 150 may provide a haptic output by moving a component of the enclosure 116 relative to other components of the enclosure or the electronic device 100. For example, the haptic device 150 may oscillate, vibrate, translate, and/or rotate the contact member 182 relative to the housing member 180 and/or the cover 118 to provide a haptic output at the rear external surface 190b. In some cases, the contact member 182 and/or the housing member 180 may be positioned so that they are likely to be in contact with a user when the device 100 is being used. Movement of the contact member 182 relative to the housing member 180 against the user's skin may produce a haptic output that can be perceived by the user. In some cases, the haptic device translates or oscillates the contact member 182 along a path that is parallel to an external surface of the electronic device (e.g., the front external surface 190a or the rear external surface 190b). In some cases, the haptic device translates or oscillates the contact member 182 along a path that is perpendicular to an external surface of the electronic device (e.g., the front external surface 190a or the rear external surface 190b).

In some cases, the contact member 182 is configured to rotate relative to the housing member 180 or the cover 118. For example, the contact member 182 may have a round (e.g., circular) perimeter and the contact member 182 may be positioned in a round opening in the housing member 180. The contact member 182 may rotate relative to the housing member 180, for example as shown with respect to FIGS. 5A-5C. Rotation of the contact member 182 relative to the housing member 180 against the user's skin may produce a haptic output that can be perceived by the user. In some cases, the contact member 182 moving (e.g., rotating) relative to the housing member 180 produces a shear force on the user's skin, which may be perceived differently or give a different sensation than a vibration or translation of the contact member 182.

In some cases, the haptic device 150 may provide a haptic output by deflecting a portion of the enclosure 116. For example, the haptic device 150 may deflect a portion of the housing member 180 inward and/or outward to provide a haptic output at the rear external surface 190b. In some cases, the enclosure 116 does not include the contact member 182. For example, the contact member 182 shown in FIG. 1 may be replaced with a portion of the housing member 180 that is continuous with the rest of the housing member 180. The portion of the housing member 180 may be configured to deflect or otherwise provide a haptic output along the rear external surface 190b. Deflection or other movement of the housing member 180 against the user's skin may produce a haptic output that can be perceived by the user.

In some cases, the haptic device 150 may provide a global haptic output by moving a mass or weighted member within the enclosure 116. For example, the contact member 182 shown in FIG. 1 may be a mass or weighted member positioned within the enclosure 116. The haptic device 150 may cause the mass or weighted member to move and, in some cases, oscillate, to produce a perceptible vibration or tactile effect along an external surface of the electronic device 100.

In some cases, the haptic device 150 may provide a haptic output at the front external surface 190a by translating and/or rotating the cover 118 relative to other components of the enclosure 116, such as the housing member 180. In some cases, the haptic device 150 may provide a haptic output along a portion of the external surface of the electronic device 100 defined by one or more input devices, such as a crown 121, a button, or the like. In some cases, the haptic device 150 oscillates, vibrates, rotates, and/or translates an input device or a portion of an input device relative to one or more additional components of the electronic device 100.

In various embodiments, the haptic device 150 may be directly connected to a component of the electronic device 100 that defines an external surface of the electronic device, including the enclosure 116, an input device, or another component. In some cases, the haptic device 150 is coupled to the relevant component(s) defining the external surface by a connector 151. The connector 151 may transfer motion from the haptic device 150 to the component(s) defining the external surface to produce the haptic output along the external surface.

In some cases, the electronic device 100 includes a crown 121 configured to receive translational inputs, rotational inputs, and/or touch inputs. Inputs received at the crown 121 may result in changes in outputs provided by the electronic device 100 such as a graphical output of the display 134, and/or otherwise modify operations of the electronic device. In some cases, the crown 121 may be positioned along a side of the enclosure 116, and may extend through an opening 123 defined in the enclosure. The crown 121 may include a user-rotatable crown body 120 and a shaft 122. The crown body 120 may be positioned at least partially outside of the device enclosure 116 and may be coupled to the shaft 122. In some cases, the shaft 122 extends from the crown body 120 and extends through the opening 123.

In some cases, the device 100 may include a conductive portion that may be used to perform an ECG measurement. The crown body 120 or another input device 130 may define a conductive surface for receiving touch inputs. In some cases, the conductive surface functions as an electrode to sense voltages or signals indicative of one or more touch inputs and/or biological parameters, such as an electrocardiogram, of a user in contact with the conductive surface. The enclosure 116 may define a touch-sensitive or conductive surface that is electrically coupled to the processing unit 111 and also functions as an electrode. The processing unit 111 may determine an electrocardiogram using outputs of the electrodes of the crown body 120 and the enclosure 116. In various embodiments, the crown 121 is electrically isolated from the enclosure 116, for example to allow separate measurements at the electrodes. In various embodiments, the crown body 120 may be electrically coupled to the processing unit 111 or another circuit of the electronic device 100, for example via a connector 136b and/or the shaft 122.

In various embodiments, the display 134 may be positioned at least partially within the enclosure 116. The display 134 provides a graphical output, for example associated with an operating system, user interface, and/or applications of the electronic device 100. In one embodiment, the display 134 includes one or more sensors and is configured as a touch-sensitive (e.g., single-touch, multi-touch) and/or force-sensitive display to receive inputs from a user. The display 134 is operably coupled to the processing unit 111 of the electronic device 100, for example by a connector 136c. In some cases, the graphical output of the display 134 is visible along the front external surface 190a.

In various embodiments, a graphical output of the display 134 is responsive to inputs provided at the crown 121, the display, or another input device 130. For example, the processing unit 111 may be configured to modify the graphical output of the display 134 in response to determining an electrocardiogram, receiving rotational inputs, receiving translational inputs, or receiving touch inputs. In some cases, a haptic output provided by the haptic device 150 corresponds to the graphical output of the display 134. In some cases, the haptic device 150 may produce a haptic output that is coordinated with a change in the graphical output of the display 134. For example, the haptic output may be produced at or near the same time as the change in the graphical output of the display 134. In some cases, a time that the haptic output is produced overlaps a time that the graphical output of the display 134 changes.

The display 134 can be implemented with any suitable technology, including, but not limited to, liquid crystal display (LCD) technology, light emitting diode (LED) technology, organic light-emitting display (OLED) technology, organic electroluminescence (OEL) technology, or another type of display technology. In some cases, the display 134 is positioned beneath and viewable through the cover 118.

Broadly, the input devices 130 may detect various types of input, and the output devices 132 may provide various types of output. The processing unit 111 may be operably coupled to the input devices 130 and the output devices 132, for example by connectors 136d and 136e. The processing unit 111 may receive input signals from the input devices 130, in response to inputs detected by the input devices. The processing unit 111 may interpret input signals received from one or more of the input devices 130 and transmit output signals to one or more of the output devices 132. The output signals may cause the output devices 132 to provide one or more outputs. Detected input at one or more of the input devices 130 may be used to control one or more functions of the device 100. In some cases, one or more of the output devices 132 may be configured to provide outputs that are dependent on, or manipulated in response to, the input detected by one or more of the input devices 130. The outputs provided by one or more of the output devices 132 may also be responsive to, or initiated by, a program or application executed by the processing unit 111 and/or an associated companion device. Examples of suitable processing units, input devices, output devices, and displays, are discussed in more detail below with respect to FIG. 12.

Figure 2A:
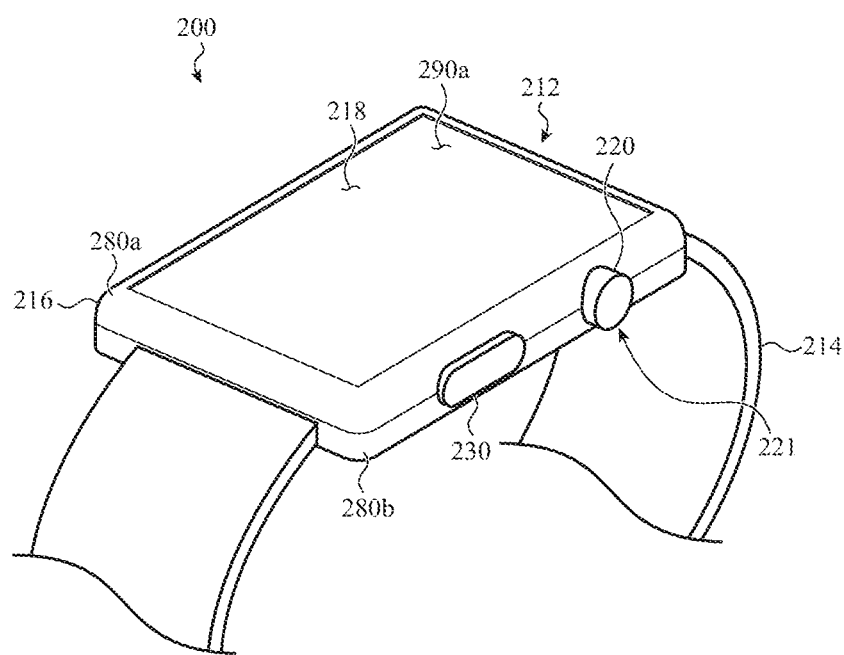
FIGS. 2A-2B show an example of an electronic watch that may incorporate a haptic device with an actuation member formed from a shape-memory alloy material and a restoration mechanism.
Figure 2B:
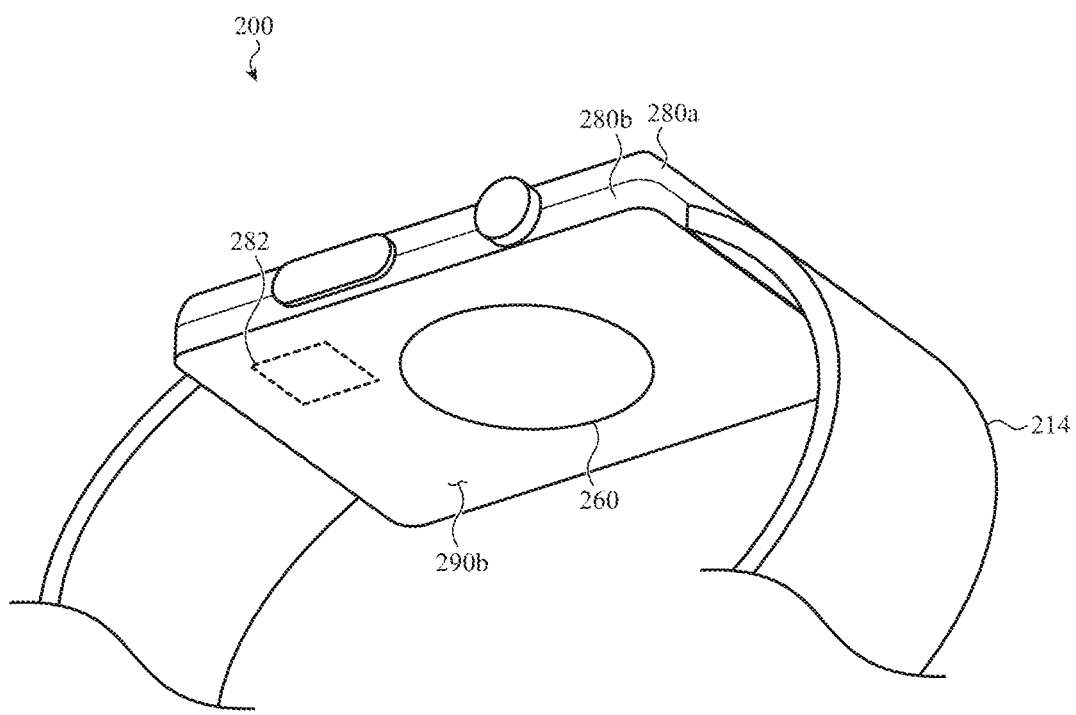

FIGS. 2A-2B show an example of an electronic watch 200 that may incorporate a haptic device with an actuation member formed from a shape-memory alloy material and a restoration mechanism. The structure and functionality of the electronic watch 200 may be similar to the structure and functionality of the electronic watch 100 discussed above with respect to FIG. 1. Other devices that may incorporate the haptic devices described herein include other wearable electronic devices, other timekeeping devices, other health monitoring or fitness devices, other portable computing devices, mobile phones (including smart phones), tablet computing devices, digital media players, virtual reality devices, audio devices (including earbuds and headphones), and the like.

The electronic watch 200 may include a watch body 212 and a watch band 214. The watch body 212 may include an enclosure 216. As noted above, in some cases, the haptic device of the electronic watch 200 provides haptic outputs that may be felt along one or more portions of the enclosure 216. The enclosure 216 may contain one or more components of the electronic watch 200 and may define at least part of an external surface of the electronic watch. The haptic device may provide haptic outputs along one or more portions of the external surface defined by the enclosure 216.

In some cases, the enclosure 216 defines a front external surface 290a (shown in FIG. 2A) that faces away from a user's skin when the watch 200 is worn by a user and a rear external surface 290b (shown in FIG. 2B) that faces toward the user's skin (e.g., opposite the front external surface 290a). In some cases, the haptic device of the electronic watch provides haptic outputs at an area 282 along the rear external surface 290b of the watch.

In some cases, the area 282 may be defined by a separate component that is capable of rotating and/or translating relative to other components of the electronic watch 200 (e.g., similar to contact member 182 above) to provide haptic outputs. Alternatively, the area 282 may be a portion of a larger component of the enclosure 216 that deflects or otherwise moves to provide haptic outputs.

In some cases, the enclosure 216 may include a housing member 280. In some cases, at least a portion of the housing member 280 faces toward a user's skin when the watch 200 is worn. Alternatively, the enclosure 216 may include two or more housing members. For example, the enclosure 216 may include a front housing member that faces away from a user's skin when the watch 200 is worn by a user, and a rear housing member that faces toward the user's skin. In some cases, haptic outputs are provided at the housing member 280 and may be tactilely perceived by a body part of the user that is in contact with the electronic watch 200. The one or more housing members may be metallic, plastic, ceramic, glass, or other types of housing members (or combinations of such materials).

In some cases, as shown in FIG. 2B, the enclosure 216 may include a contact member (e.g., a rear cover 260). In some cases, the haptic device provides haptic outputs at the rear cover 260. In some cases, the haptic device may cause the rear cover 260 to move relative to the housing member 280, the cover 218, and/or other components of the electronic watch 200.

In some cases, the rear cover 260 is positioned over and/or within an opening defined in the housing member 280. The rear cover 260 may be capable of rotating and/or translating relative to the housing member 280 to provide haptic outputs.

In some cases, the rear cover 260 is positioned over one or more additional components of the electronic watch 200. For example, in some cases, the electronic watch 200 includes a wireless charging coil positioned beneath the rear cover 260, and the rear cover 260 is capable of transmitting wireless charging signals from a wireless charger external to the enclosure 216 and through the rear cover 260 to the wireless charging coil. In some cases, the rear cover 260 is formed of a material that is suitable for transmitting wireless charging signals, including plastic, ceramic, or glass.

In some cases, the electronic watch 200 includes one or more biosensors positioned beneath the rear cover 260, for example to detect a biological parameter (e.g., a heart rate) of a user. In some cases, the biosensors include optical heart rate sensors that transmit optical signals through the rear cover 260 to a user's skin, and receive reflected optical signals through the rear cover that may be processed to determine the biological parameter(s). In some cases, the rear cover 260 is formed of a material that is suitable for transmitting optical signals, including plastic, ceramic, or glass.

In some cases, the rear cover 260 may have one or more conductive electrodes positioned thereon. The one or more electrodes on the additional cover may be used to determine a biological parameter, such as a heart rate, an ECG, or the like. In some cases, the electrodes are used in combination with one or more additional electrodes, such as a surface of a crown or other input device. In some cases, the electronic watch 200 includes two electrodes positioned along a rear surface of the electronic watch 200 (e.g., along a surface of the rear cover 260) and the electrodes may be configured to contact a wrist of the user. A third conductive electrode may be positioned along another surface of the electronic watch 200 (e.g., along the enclosure 216, the crown 221, and/or the button 230) and may be configured to be contacted by a finger or other portion of the user's body in order to facilitate an ECG or other heart- or health-related measurement.

Returning to FIG. 2A, in some cases, the enclosure 216 may include a cover 218 facing away from a user's skin as the watch 200 is worn. In some cases, the cover 218 is mounted to or coupled to the housing member 280. The cover 218 and/or portions of the housing member 280 may define the front external surface 290a of the electronic watch 200. In some cases, the haptic device may be coupled to the cover 218 and may be capable of providing haptic outputs at the front external surface 290a.

The cover 218 may be positioned over and protect a display mounted within the enclosure 216 (e.g., display 134 of FIG. 1). The display may be viewable by a user through the cover 218. In some cases, the cover 218 may be part of a display stack, which may include touch sensing or force sensing capability. The display may be configured to depict a graphical output of the watch 200, and a user may interact with the graphical output (e.g., using a finger, stylus, or other pointer). As one example, the user may select (or otherwise interact with) a graphic, icon, or the like presented on the display by touching or pressing (e.g., providing touch input) on the display at the location of the graphic. In some cases, the haptic outputs provided by the haptic device correspond to the graphical output of the display and/or inputs received via the display.

As used herein, the term "cover" may be used to refer to any transparent, semi-transparent, or translucent surface made out of glass, a crystalline material (such as sapphire or zirconia), plastic, or the like. Thus, it should be appreciated that the term "cover," as used herein, encompasses amorphous solids as well as crystalline solids. In some examples, the cover 218 may be a sapphire cover. The cover 218 may also be formed of glass, plastic, or other materials.

The watch body 212 may include at least one input device or selection device, such as a crown, scroll wheel, knob, dial, button, or the like, which may be operated by a user of the watch 200. In some embodiments, the watch 200 includes a crown 221 that includes a crown body 220 and a shaft (not shown in FIG. 2A). The enclosure 216 may define an opening through which the shaft extends. The crown body 220 may be attached and/or coupled to the shaft, and may be accessible to a user exterior to the enclosure 216.

The crown body 220 may be user-rotatable, and may be manipulated (e.g., rotated, pressed) by a user to rotate or translate the shaft. The shaft may be mechanically, electrically, magnetically, and/or optically coupled to components within the enclosure 216. A user's manipulation of the crown body 220 and shaft may be used, in turn, to manipulate or select various elements displayed on the display, to adjust a volume of a speaker, to turn the watch 200 on or off, and so on. The crown body 220 may be operably coupled to a circuit within the enclosure 216 (e.g., a processing unit), but electrically isolated from the enclosure 216. As discussed above, the crown 221 may include a conductive electrode used to measure an ECG or other health-related measurement.

The enclosure 216 may also include an opening through which a button 230 protrudes. In some embodiments, the input devices (e.g., the crown body 220, scroll wheel, knob, dial, button 230, or the like) may be touch sensitive, conductive, and/or have a conductive surface, and a signal route may be provided between the conductive portion of the input device and a circuit within the watch body 212. In some cases, the haptic device may be coupled to an input device and may be capable of providing haptic outputs at one or more portions of the external surface of the watch 200 defined by the input device. In some cases, the haptic outputs provided by the haptic device correspond to the inputs received via the input device.

The enclosure 216 may include structures for attaching the watch band 214 to the watch body 212. In some cases, the structures may include elongate recesses or openings through which ends of the watch band 214 may be inserted and attached to the watch body 212. In other cases (not shown), the structures may include indents (e.g., dimples or depressions) in the enclosure 216, which indents may receive ends of spring pins that are attached to or threaded through ends of a watch band to attach the watch band to the watch body.

The watch band 214 may be used to secure the watch 200 to a user, another device, a retaining mechanism, and so on. In some cases, the haptic device may be coupled to the watch band 214 and may be capable of providing haptic outputs at one or more portions of the external surface of the watch 200 defined by the watch band.

In some cases, a haptic device of the electronic watch 200 may provide a global haptic output by moving a mass or weighted member within the enclosure 216. The haptic device may cause the mass or weighted member to move and, in some cases, oscillate, to produce a perceptible vibration or tactile effect along an external surface of the electronic watch 200.

In some examples, the watch 200 may lack any or all of the cover 218, the display, the crown 221, or the button 230. For example, the watch 200 may include an audio input or output interface, a touch input interface, a force input or haptic output interface, or other input or output interface that does not require the display, crown 221, or button 230. The watch 200 may also include the aforementioned input or output interfaces in addition to the display, crown 221, or button 230. When the watch 200 lacks the display, the front side of the watch 200 may be covered by the cover 218, or by a metallic or other type of housing member.

As noted above, the haptic devices discussed herein may include an actuation member formed at least partially from an SMA material that changes shape (e.g., expands or contracts) in response to an applied current and a restoration mechanism that restores the SMA actuation member to its original shape or to a similar shape. The change in the shape of the SMA actuation member and the restoration of the shape of the SMA actuation member may combine to produce a haptic output at the electronic watch 200.

Figure 3A:
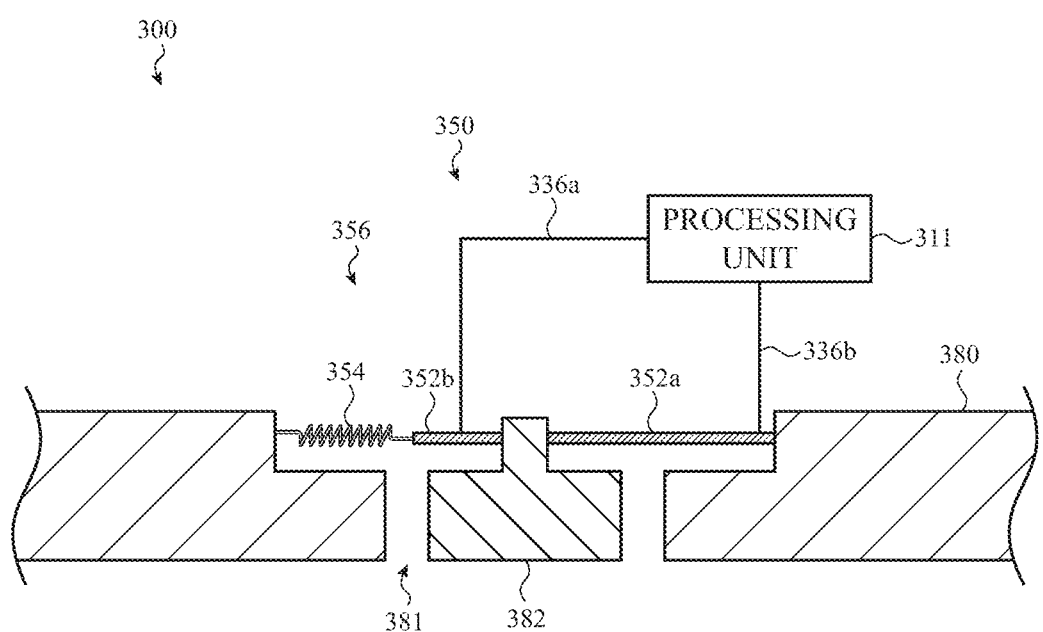
FIGS. 3A-3C show functional block diagrams of an example haptic device having an SMA actuation member and a restoration mechanism installed in an example electronic device.
Figure 3B:
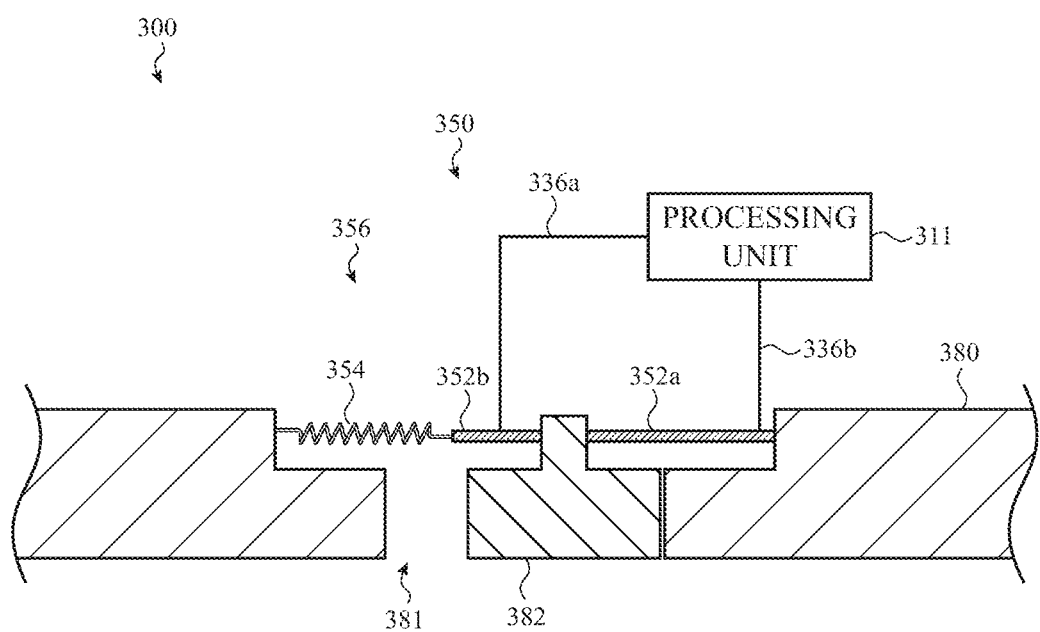
Figure 3C:
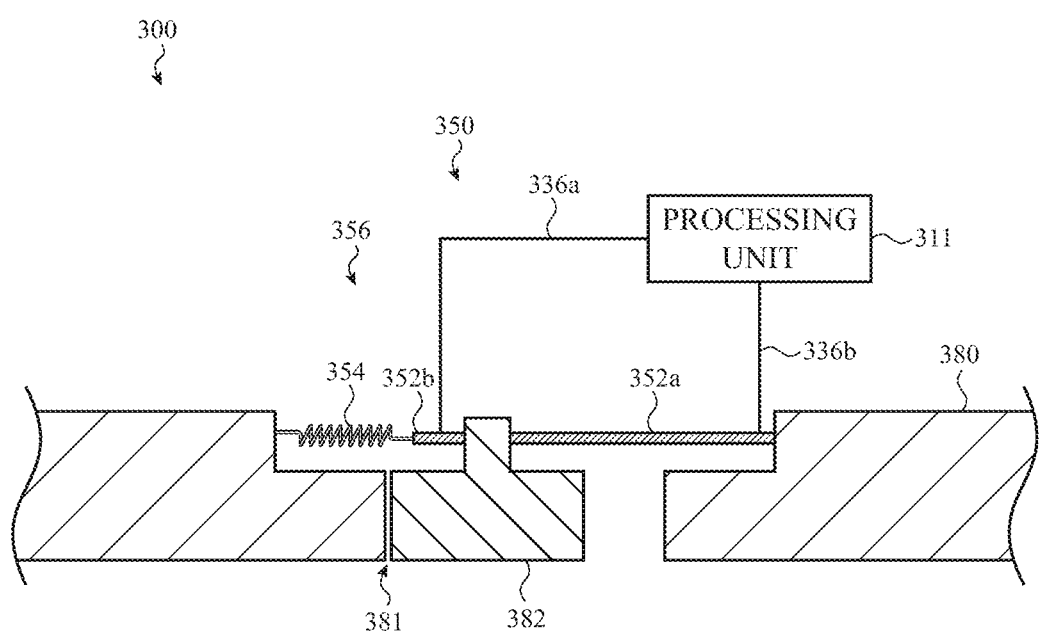

FIGS. 3A-3C show functional block diagrams of an example haptic device 350 having an SMA actuation member 352a and a restoration mechanism 356, installed in an example electronic device 300. The example electronic device 300 of FIGS. 3A-3C may have similar structure, components, and functionality as other electronic devices discussed herein. FIG. 3A illustrates a contact member 382 positioned in an opening 381 of a housing member 380. The contact member 382 and/or the housing member 380 may define an external surface of the electronic device. In some cases, the haptic device 350 causes the contact member 382 to translate or oscillate laterally (e.g., left to right and right to left with respect to FIG. 3A) relative to the housing member 380. In some cases, the lateral translation or oscillation is along a path that is parallel to an external surface of the electronic device (e.g., the front external surface or the rear external surface). The translation or oscillation may produce a vibration or tactile effect along the external surface of the electronic device 300.

In some cases, the haptic device 350 includes an SMA actuation member 352a and a restoration mechanism 356. The SMA actuation member 352a and the restoration mechanism 356 may couple the contact member 382 to other components of the electronic device. In some cases, the SMA actuation member 352a is positioned between and coupled to a first side of the contact member 382 and the housing member 380. In some cases, the restoration mechanism 356 is positioned between and coupled to a second, opposite side of the contact member 382 and the housing member 380.

In some cases, the SMA actuation member 352a contracts from a first shape having a first length to a second shape having a second, shorter length in response to a signal received from the processing unit 311, and, after the contraction, the restoration mechanism 356 elongates the SMA actuation member 352a to the first shape or a similar shape (e.g., a third shape having a length between the length of the first shape and the length of the second shape).

FIG. 3A shows the contact member 382 in a first position. In some cases, the first position is a default position of the contact member 382. In some cases, in the first position, the contact member 382 is evenly spaced between walls of the opening 381. The contact member 382 may be flush with the external surface of the housing member 380, or it may be recessed or protruding relative to the external surface.

In some cases, the SMA actuation member 352a is responsive to a signal from the processing unit 311, which may cause a current or other electrical signal to be applied to the SMA actuation member 352a, thereby causing the SMA actuation member 352a to contract. As shown in FIG. 3B, contraction of the SMA actuation member 352a may cause the contact member 382 to translate rightward from the first position shown in FIG. 3A to a second position shown in FIG. 3B. The spring 354 may expand to allow the movement of the contact member 382 to the second position as shown in FIG. 3B. The rightward translation of the contact member 382 may produce a first portion of a haptic output.

As discussed previously, the restoration mechanism 356 may include an SMA member. In the present example, the restoration mechanism 356 includes a second SMA actuation member 352*b* and a spring 354 coupled together in series. The SMA actuation members 352*a* and 352*b* may be electrically coupled to a processing unit 311 (e.g., by connectors 336*a* and 336*b*) and configured to contract in response to receiving signals from the processing unit 311.

In the present example and in many of the examples described herein, the restoration mechanism 356 may include both a spring 354 and a second SMA actuation member 352*b*. Alternatively, the spring 354 may be omitted and the restoration mechanism 356 may rely primarily on the second SMA actuation member 352*b* to provide a restoration force to the first SMA actuation member 352*a*.

As noted above, in many cases, the time required for elongation of the SMA actuation member 352*a* is sufficiently long that it limits the number of successive contractions and elongations that can occur in a given time period. In some cases, the restoration mechanism 356 elongates the SMA actuation member 352*a* after the contraction to prepare the SMA actuation member 352*a* for a subsequent contraction. Following the application of the current to the SMA actuation member 352*a*, the applied current is ceased, which allows the SMA actuation member 352*a* to begin elongating back to the first shape or a similar shape. At this point, the spring 354 may also begin to contract, which exerts a tensile force on the SMA actuation member 352*a*. In some cases, an additional signal is applied to the second SMA actuation member 352*b*, causing the second SMA actuation member to contract, which exerts an additional tensile force on the first SMA actuation member 352*a*. The tensile force(s) may accelerate or otherwise assist the elongation of the SMA actuation member 352*a*, causing the SMA actuation member 352*a* to elongate faster and/or more completely than if no tensile force was applied.

As the restoration mechanism 356 elongates the SMA actuation member 352*a*, the contact member 382 may move from right to left with respect to FIG. 3B. In some cases, the leftward translation of the contact member 382 may produce a second portion of the haptic output. In some cases, the restoration mechanism 356 returns the contact member 382 to the first position shown in FIG. 3A. In other cases, the restoration mechanism 356 may move the contact member 382 to a third position to the left of the first position, as shown in FIG. 3C.

In various embodiments, once the SMA actuation member 352*a* has been elongated (either partially or fully), it may be subsequently contracted in response to receiving another signal from the processing unit 311 and subsequently elongated by the restoration mechanism 356. Contraction and elongation may be repeated to repeatedly move the contact member 382 in alternating directions (e.g., left to right and right to left with respect to FIGS. 3A-3C) to produce one or more haptic outputs and/or portions thereof.

In various embodiments, a compliant member may be disposed between the contact member 382 and the housing member 380. The compliant member may form a seal between the contact member 382 and the housing member 380 to exclude contaminants from the interior of the electronic device, while still allowing the contact member 382 to move relative to the housing member 380 to produce a haptic output.

In some cases, either of the spring 354 or the SMA actuation member 352*b* may be omitted from the restoration mechanism 356. The directions of movement described with respect to FIGS. 3A-3C are examples for illustrative purposes only. In various embodiments, the directions of movement may be different from those described.

Figure 4A:
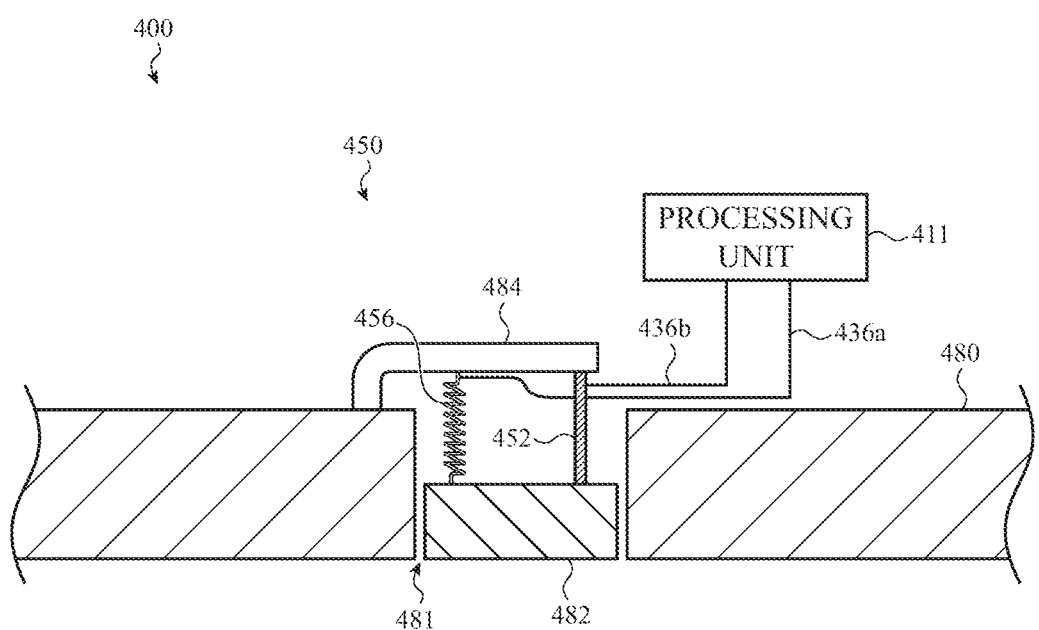
FIGS. 4A-4C show functional block diagrams of an example haptic device having an SMA actuation member and a restoration mechanism installed in an example electronic device.
Figure 4B:
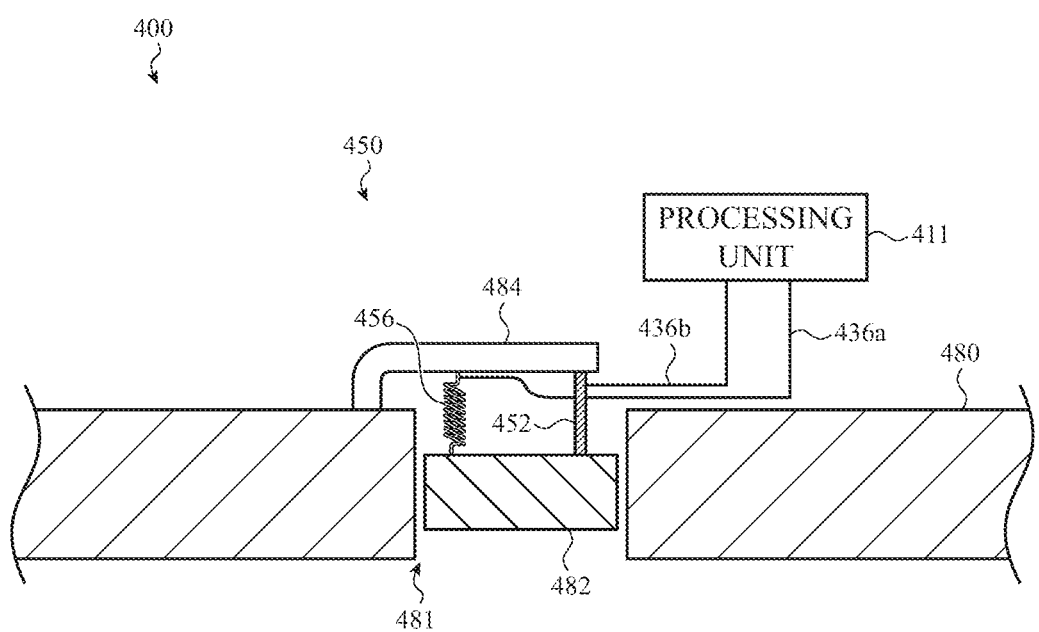
Figure 4C:
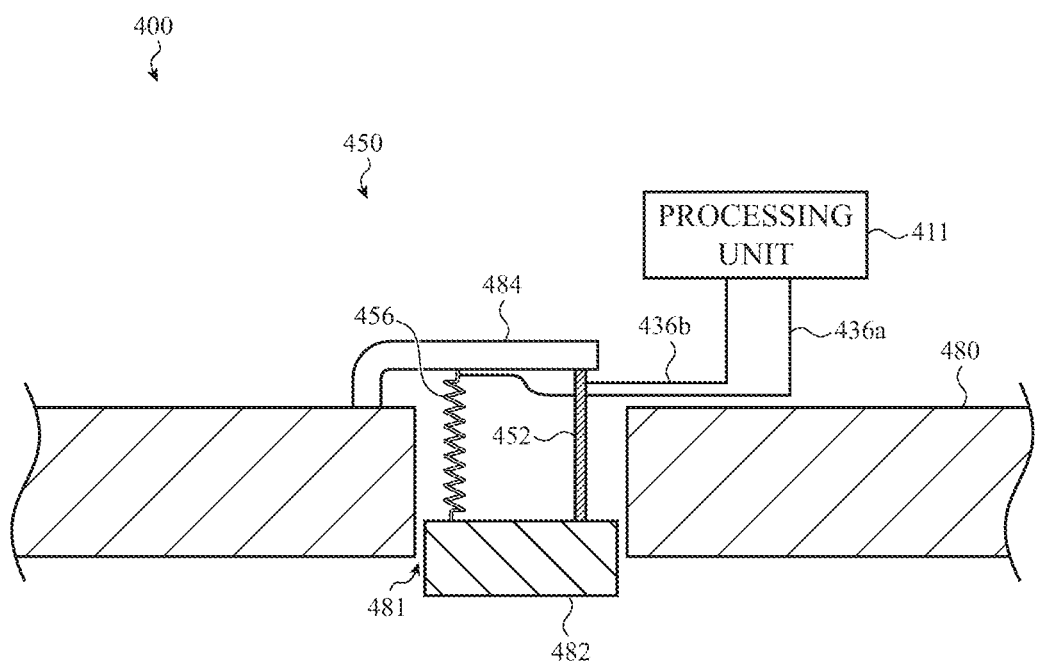

FIGS. 4A-4C show functional block diagrams of an example haptic device 450 having an SMA actuation member 452 and a restoration mechanism 456, installed in an example electronic device 400. The example electronic device 400 of FIGS. 4A-4C may have similar structure, components, and functionality as other electronic devices discussed herein. FIG. 4A illustrates a contact member 482 positioned in an opening 481 of a housing member 480. In some cases, the haptic device 450 causes the contact member 482 to translate or oscillate in and out of the opening 481 (e.g., up and down with respect to FIG. 4A) relative to the housing member 480 to provide a haptic output. In some cases, the translation or oscillation is along a path that is perpendicular to an external surface of the electronic device (e.g., the front external surface of the rear external surface). The translation may cause the contact member 482 to protrude from and/or be recessed with respect to the housing member 480. The translation or oscillation may produce a vibration or tactile effect along the external surface of the electronic device 400.

In some cases, the haptic device 450 includes an SMA actuation member 452 and a restoration mechanism 456. The SMA actuation member 452 and the restoration mechanism 456 may couple the contact member 482 to other components of the electronic device. In some cases, the SMA actuation member 452 and the restoration mechanism 456 are positioned between and coupled to a first side of the contact member 482 and a support member 484. The support member 484 may be a portion of the housing member 480 or may be attached to the housing member 480.

In some cases, the SMA actuation member 452 is responsive to a signal produced by the processing unit 411, which causes a current to be applied to the SMA actuation member 452, thereby causing the SMA actuation member 452 to contract. As shown in FIG. 4B, contraction of the SMA actuation member 452 may cause the contact member 482 to translate upward from the first position shown in FIG. 4A to a second position shown in FIG. 4B. The upward translation of the contact member 482 may produce a first portion of a haptic output. FIG. 4A shows the contact member 482 in a first position. In some cases, the first position is a default position of the contact member 482.

In some cases, the SMA actuation member 452 contracts from a first shape having a first length to a second shape having a second, shorter length in response to a signal received from the processing unit 411, and, after the contraction, the restoration mechanism 456 elongates the SMA actuation member 452 to the first shape or a similar shape (e.g., a third shape having a length between the length of the first shape and the length of the second shape). The SMA actuation member 452 may be electrically coupled to a processing unit 411 (e.g., by connectors 436*a* and 436*b*) and configured to contract in response to receiving signals from the processing unit 411.

As noted above, in many cases, the time required for elongation of the SMA actuation member 452 is sufficiently long that it limits the number of successive contractions and elongations that can occur in a given time period. In some cases, the restoration mechanism 456 elongates the SMA actuation member 452 after the contraction to prepare the SMA actuation member 452 for a subsequent contraction.

Following the application of the current to the SMA actuation member 452, the applied current is ceased, which allows the SMA actuation member to begin elongating back to the first shape or to a similar shape.

In some cases, the restoration mechanism 456 includes a spring that is compressed as the contact member 482 translates upward (e.g., as shown in FIG. 4B). The spring may exert a downward force on the contact member 482, which in turn applies a tensile force on the SMA actuation member. In some cases, the restoration mechanism 456 includes an SMA actuation member that expands or elongates in response to an applied current. The expansion of the SMA actuation member may exert a downward force on the contact member 482, which in turn applies a tensile force on the SMA actuation member. The tensile force(s) may accelerate the elongation of the SMA actuation member 452, causing the SMA actuation member to elongate faster and/or more completely than if no tensile force was applied.

In the present example and in many of the examples described herein, the restoration mechanism 456 may include a spring, a spring and a second SMA actuation member, or a second SMA actuation member without a spring. As discussed previously, the spring may be omitted and the restoration mechanism 456 may rely primarily the second SMA actuation member to provide a restoration force to the (first) SMA actuation member 452. Similar to the (first) SMA actuation member 452, a second SMA actuation member of the restoration mechanism 456 may be responsive to a signal produced by the processing unit 411, which causes a drive current or other electrical signal to alter a shape and/or length of the second SMA actuation member.

As the restoration mechanism 456 elongates the SMA actuation member 452, the contact member 482 may move downward with respect to FIG. 4B. In some cases, the downward translation of the contact member 482 may produce a second portion of the haptic output. In some cases, the restoration mechanism 456 returns the contact member 482 to the first position shown in FIG. 4A. In other cases, the restoration mechanism 456 may move the contact member 482 to a third position below the first position, as shown in FIG. 4C.

In various embodiments, once the SMA actuation member 452 has been elongated (either partially or fully), it may be subsequently contracted in response to receiving another signal from the processing unit 411 and subsequently elongated by the restoration mechanism 456. Contraction and elongation may be repeated to repeatedly move the contact member 482 up and down to produce one or more haptic outputs and/or portions thereof.

In various embodiments, a compliant member may be disposed between the contact member 482 and the housing member 480. The compliant member may form a seal between the contact member 482 and the housing member 480 to exclude contaminants from the interior of the electronic device, while still allowing the contact member 482 to move relative to the housing member 480 to produce a haptic output.

The directions of movement described with respect to FIGS. 4A-4C are examples for illustrative purposes only. In various embodiments, the directions of movement may be different from those described.

Figure 5A:
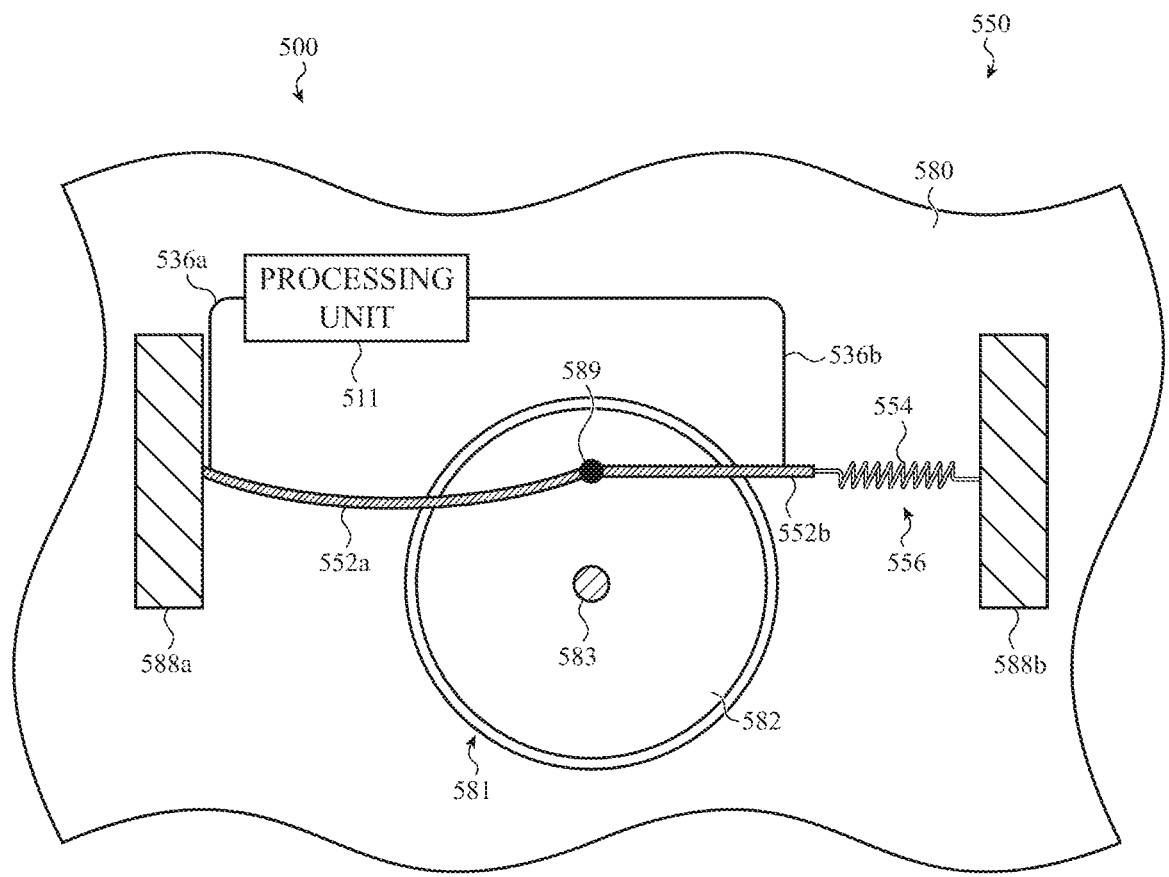
FIGS. 5A-5C show functional block diagrams of an example haptic device having an SMA actuation member and a restoration mechanism installed in an example electronic device.
Figure 5B:
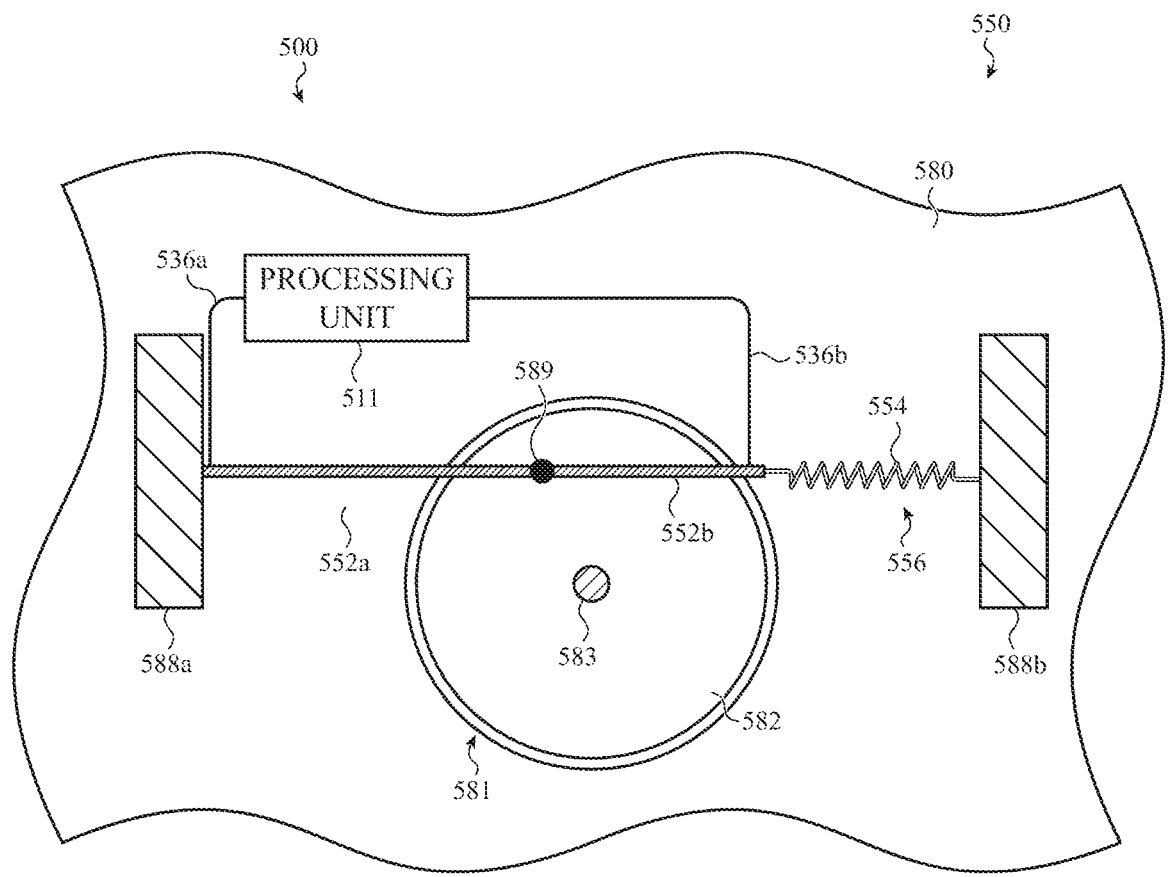
Figure 5C:
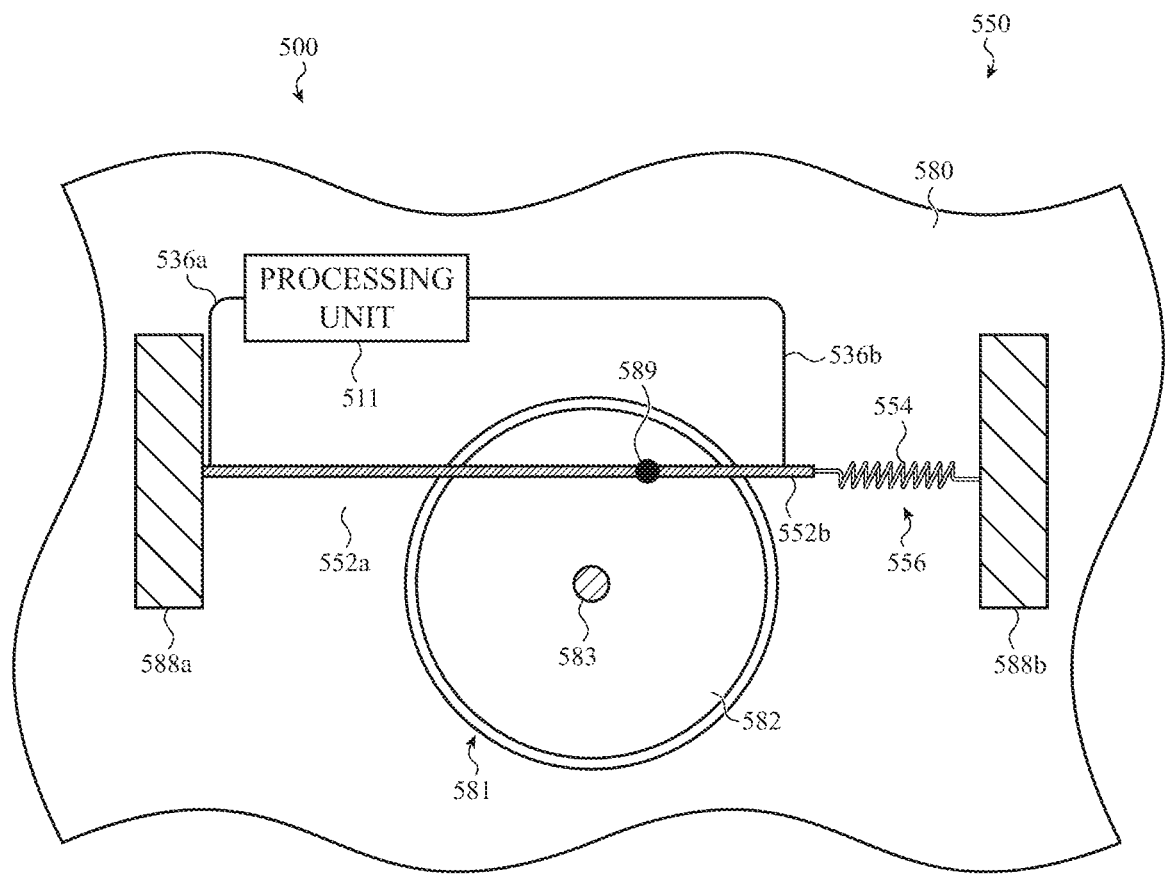

FIGS. 5A-5C show functional block diagrams of an example haptic device 550 having an SMA actuation member 552a and a restoration mechanism 556, installed in an example electronic device 500. The example electronic device 500 of FIGS. 5A-5C may have similar structure, components, and functionality as other electronic devices discussed herein. FIG. 5A illustrates a contact member 582 positioned in an opening 581 of a housing member 580. In some cases, the haptic device 550 causes the contact member 582 to rotate (e.g., clockwise and counter-clockwise with respect to FIG. 5A) with respect to the housing member 580 to provide a haptic output. In some cases, the contact member 582 rotates around an axle 583 that is fixed with respect to the housing member 580. The rotation may produce a vibration or tactile effect along the external surface of the electronic device 500.

In some cases, the haptic device 550 includes an SMA actuation member 552a and a restoration mechanism 556. The SMA actuation member 552a and the restoration mechanism 556 may couple the contact member 582 to other components of the electronic device. In some cases, the SMA actuation member 552a is coupled to and positioned between a support member 588a of the electronic device and a connection point 589 of the contact member 582. In some cases, the restoration mechanism 556 is coupled to and positioned between a support member 588b and the connection point 589 of the contact member 582. The support members 588a and 588b may be portions of the housing member 580 or may be attached to the housing member 580 or another component of the electronic device.

In some cases, the SMA actuation member 552a contracts from a first shape having a first length to a second shape having a second, shorter length in response to a signal received from the processing unit 511, and, after the contraction, the restoration mechanism 556 elongates the SMA actuation member 552 to the first shape or a similar shape (e.g., a third shape having a length between the length of the first shape and the length of the second shape). FIG. 5A shows the contact member 582 in a first position. In some cases, the first position is a default position of the contact member 582.

In some cases, the SMA actuation member 552a is responsive to a signal produced by the processing unit 511, which may cause a current or other electrical signal to be applied to the SMA actuation member 552a, thereby causing the SMA actuation member 552a to contract. As shown in FIG. 5B, contraction of the SMA actuation member 552a may cause the contact member 582 to rotate counter-clockwise from the first position shown in FIG. 5A to a second position shown in FIG. 5B. The spring 554 may expand to allow the movement of the contact member 582 to the second position as shown in FIG. 5B. The counter-clockwise rotation of the contact member 582 may produce a first portion of a haptic output.

The restoration mechanism 556 may include a second SMA actuation member 552b and a spring 554 coupled together in series. The SMA actuation members 552a and 552b may be electrically coupled to a processing unit 511 (e.g., by connectors 536a and 536b) and configured to contract in response to receiving signals from the processing unit 511.

In the present example and in many of the examples described herein, the restoration mechanism 556 may include a spring 554, a spring 554 and a second SMA actuation member 552b, or a second SMA actuation member 552b without a spring. As discussed previously, the spring 554 may be omitted and the restoration mechanism 556 may rely primarily on the second SMA actuation 552b member to provide a restoration force to the first SMA actuation member 552a. Similar to the first SMA actuation member 552a, the second SMA actuation member 552b of the restoration mechanism 556 may be responsive to a signal produced by the processing unit 511, which causes a drive current or other electrical signal to alter a shape and/or length of the second SMA actuation member 552b.

As noted above, in many cases, the time required for elongation of the SMA actuation member 552a is sufficiently long that it limits the number of successive contractions and elongations that can occur in a given time period. In some cases, the restoration mechanism 556 elongates the SMA actuation member 552a after the contraction to prepare the SMA actuation member 552a for a subsequent contraction. Following the application of the current to the SMA actuation member 552a, the applied current is ceased, which allows the SMA actuation member to begin elongating back to the first shape or a similar shape.

At this point, the spring 554 may also begin to contract, which exerts a tensile force on the SMA actuation member 552a. In some cases, an additional signal is applied to the second SMA actuation member 552b, causing the second SMA actuation member 552b to contract, which exerts an additional tensile force on the first SMA actuation member 552a. The tensile force(s) may accelerate the elongation of the SMA actuation member 552a, causing the SMA actuation member 552a to elongate faster and/or more completely than if no tensile force was applied.

As the restoration mechanism 556 elongates the SMA actuation member 552a, the contact member 582 may rotate clockwise. In some cases, the clockwise rotation of the contact member 582 may produce a second portion of the haptic output. In some cases, the restoration mechanism 556 returns the contact member 582 to the first position shown in FIG. 5A. In other cases, the restoration mechanism 556 may rotate the contact member 582 to a third position, as shown in FIG. 5C.

In various embodiments, once the SMA actuation member 552a has been elongated (either partially or fully), it may be subsequently contracted in response to receiving another signal from the processing unit 511 and subsequently elongated by the restoration mechanism 556. Contraction and elongation may be repeated to repeatedly move the contact member 582 in alternating directions (e.g., clockwise and counter-clockwise) to produce one or more haptic outputs and/or portions thereof.

In various embodiments, a compliant member may be disposed between the contact member 582 and the housing member 580. The compliant member may form a seal between the contact member 582 and the housing member 580 to exclude contaminants from the interior of the electronic device, while still allowing the contact member 582 to move relative to the housing member 580 to produce a haptic output.

In some cases, either of the spring 554 or the SMA actuation member 552b may be omitted from the restoration mechanism 556. The directions of movement described with respect to FIGS. 5A-5C are examples for illustrative purposes only. In various embodiments, the directions of movement may be different from those described.

Figure 6A:
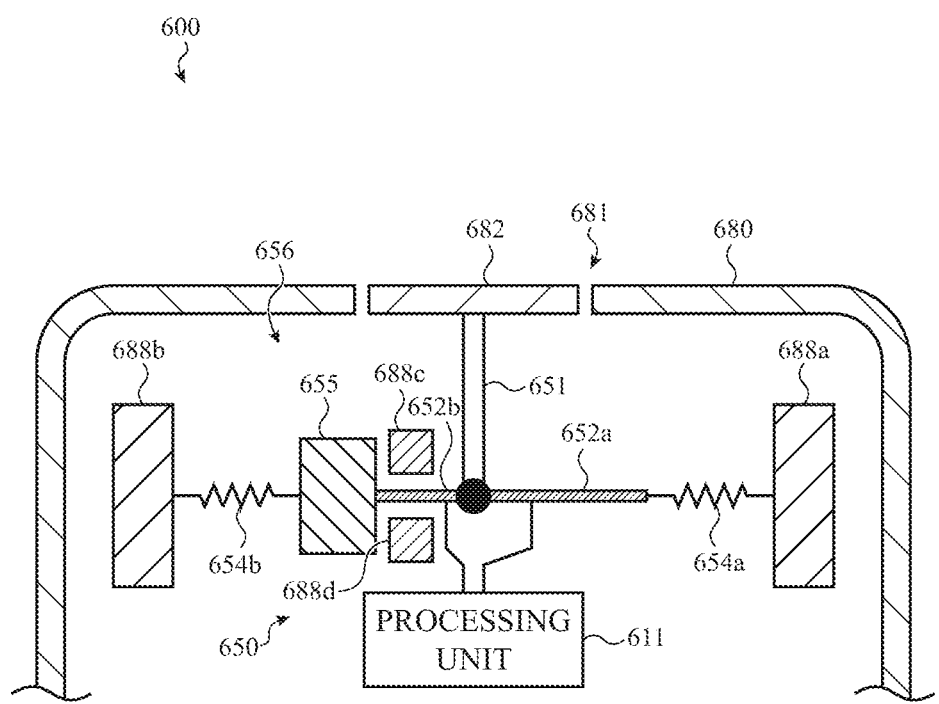
FIGS. 6A-6F show functional block diagrams of an example haptic device having an SMA actuation member and a restoration mechanism installed in an example electronic device.
Figure 6B:
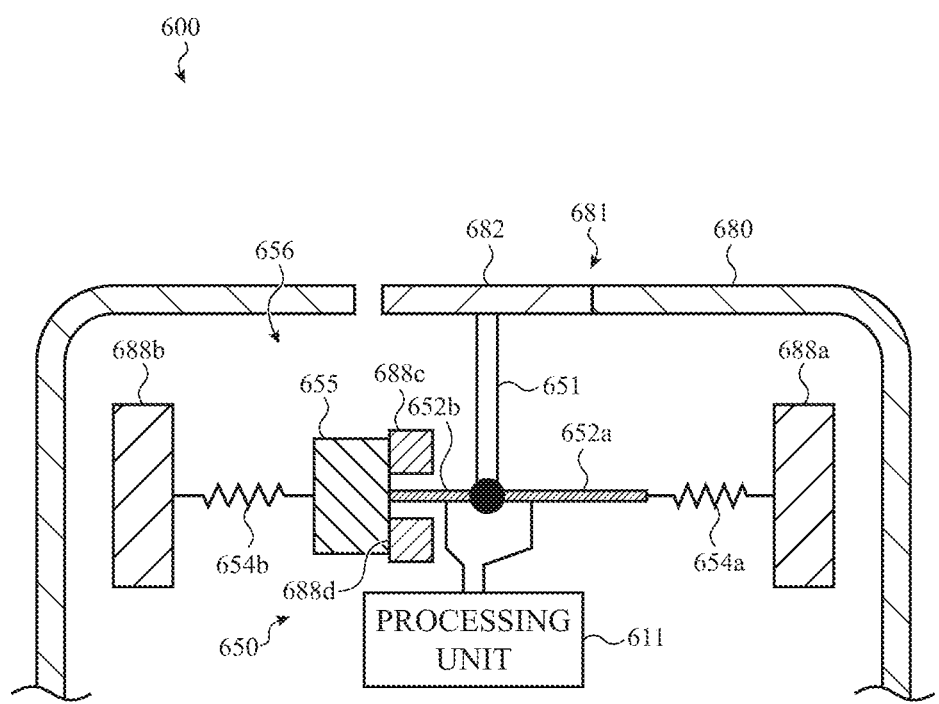
Figure 6C:
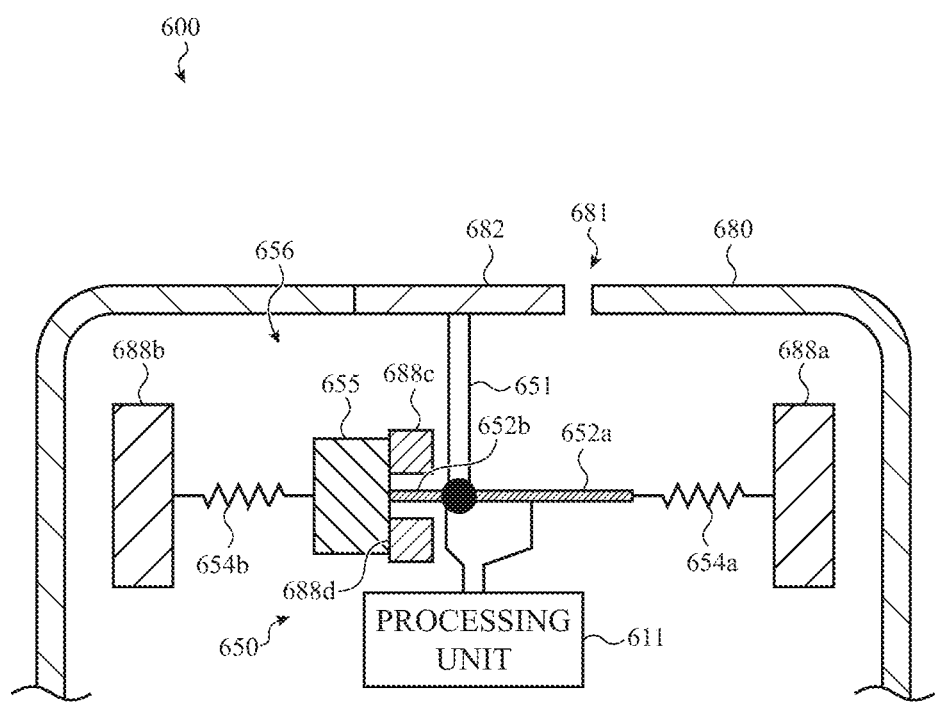

FIGS. 6A-6F show functional block diagrams of an example haptic device 650 having an SMA actuation member 652a and a restoration mechanism 656, installed in an example electronic device 600. The example electronic device 600 of FIGS. 6A-6F may have similar structure, components, and functionality as other electronic devices discussed herein. FIG. 6A illustrates a contact member 682 positioned in an opening 681 of a housing member 680. In some cases, as shown in FIGS. 6A-6C, the haptic device 650 causes the contact member 682 to translate or oscillate laterally (e.g., left to right and right to left with respect to FIG. 6A) relative to the housing member 680. In some cases, the lateral translation or oscillation is along a path that is parallel to an external surface of the electronic device (e.g., the front external surface or the rear external surface). The translation or oscillation may produce a vibration or tactile effect along the external surface of the electronic device 600.

In some cases, the haptic device 650 includes an SMA actuation member 652a and a restoration mechanism 656. The SMA actuation member 652a and the restoration mechanism 656 may couple the contact member 682 to other components of the electronic device. In some cases, the SMA actuation member 652a is coupled to a support member 688a. In some cases, a spring 654a couples the SMA actuation member 652a to the support member 688a. The SMA actuation member 652a may be coupled to a connector 651 that is attached to the contact member 682.

In some cases, the SMA actuation member 652a contracts from a first shape having a first length to a second shape having a second, shorter length in response to a signal received from the processing unit 611, and, after the contraction, the restoration mechanism 656 elongates the SMA actuation member 652a to the first shape or a similar shape (e.g., a third shape having a length between the length of the first shape and the length of the second shape).

FIG. 6A shows the contact member 682 in a first position. In some cases, the first position is a default position of the contact member 682. In some cases, in the first position, the contact member 682 is evenly spaced between walls of the opening 681. The contact member 682 may be flush with the external surface of the housing member 680, or it may be recessed or protruding relative to the external surface.

In some cases, the SMA actuation member 652a is responsive to a signal from the processing unit 611, which may cause a current or other electrical signal to be applied to the SMA actuation member 652a, thereby causing the SMA actuation member 652a to contract. As shown in FIG. 6B, contraction of the SMA actuation member 652a may cause the contact member 682 to translate rightward from the first position shown in FIG. 6A to a second position shown in FIG. 6B. The spring 654b may expand to allow the movement of the contact member 682 to the second position as shown in FIG. 6B. The rightward translation of the contact member 682 may produce a first portion of a haptic output. As the contact member 682 moves rightward with respect to FIG. 6B, the block member 655 may engage support members 688c and 688d to stop or reduce the rightward movement. The support members 688a-688d may be portions of the housing member 680 or may be attached to the housing member 680 or another component of the electronic device.

The restoration mechanism 656 may include a second SMA actuation member 652b and a second spring 654b coupled together in series. In some cases, the restoration mechanism 656 includes a block member 655 positioned between the second SMA actuation member 652b and the second spring 654b. The SMA actuation members 652a and 652b may be electrically coupled to a processing unit 611 (e.g., by connectors 636a and 636b) and configured to contract in response to signals from the processing unit 611. As mentioned previously, the SMA actuation members 652a and 652b may be driven by drive circuitry that is configured to produce the electrical current or other electrical signal required to alter the shape and/or length of the SMA actuation members 652a and 652b. Thus, it is not necessary that the SMA actuation members 652a and 652b be driven directly by the processing unit 611.

In the present example and in many of the examples described herein, the restoration mechanism 656 may include a spring 654b, a spring 654b and a second SMA actuation member 652b, or a second SMA actuation member 652b without a spring 654b. As discussed previously, the spring 654b may be omitted and the restoration mechanism 656 may rely primarily on the second SMA actuation 652b member to provide a restoration force to the first SMA actuation member 652a. Similar to the first SMA actuation member 652a, the second SMA actuation member 652b of the restoration mechanism 656 may be responsive to a signal produced by the processing unit 611, which causes a drive current or other electrical signal to alter a shape and/or length of the second SMA actuation member 652b.

As noted above, in many cases, the time required for elongation of the SMA actuation member 652a is sufficiently long that it limits the number of successive contractions and elongations that can occur in a given time period. In some cases, the restoration mechanism 656 elongates the SMA actuation member 652a after the contraction to prepare the SMA actuation member 652a for a subsequent contraction.

Following the application of the current to the SMA actuation member 652a, the applied current is ceased, which allows the SMA actuation member 652a to begin elongating back to the first shape or a similar shape. At this point, the spring 654b may also begin to contract, which exerts a tensile force on the SMA actuation member 652a. In some cases, an additional signal is applied to the second SMA actuation member 652b, causing the second SMA actuation member to contract, which exerts an additional tensile force on the first SMA actuation member 652a. The tensile force(s) may accelerate the elongation of the SMA actuation member 652a, causing the SMA actuation member 652a to elongate faster and/or more completely than if no tensile force was applied.

As the restoration mechanism 656 elongates the SMA actuation member 652a, the contact member 682 may move from right to left with respect to FIG. 6B. In some cases, the leftward translation of the contact member 682 may produce a second portion of the haptic output. In some cases, the restoration mechanism 656 returns the contact member 682 to the first position shown in FIG. 6A. In other cases, the restoration mechanism 656 may move the contact member 682 to a third position to the left of the first position, as shown in FIG. 6C. In some cases, a spring 654a is positioned between the SMA actuation member 652a and the support member 688a. The spring 654a may expand as the second SMA actuation member 652b contracts to allow the contact member 682 to move farther to the left. In some cases, the spring 654a may exert a tensile force on the SMA actuation members 652a and 652b to elongate the SMA actuation members.

In various embodiments, once the SMA actuation member 652a has been elongated (either partially or fully), it may be subsequently contracted in response to receiving another signal from the processing unit 611 and subsequently elongated by the restoration mechanism 656. Contraction and elongation may be repeated to repeatedly move the contact member 682 in alternating directions (e.g., left to right and right to left with respect to FIGS. 6A-6C) to produce one or more haptic outputs and/or portions thereof.

In various embodiments, a compliant member may be disposed between the contact member 682 and the housing member 680. The compliant member may form a seal between the contact member 682 and the housing member 680 to exclude contaminants from the interior of the electronic device, while still allowing the contact member 682 to move relative to the housing member 680 to produce a haptic output.

Figure 6D:
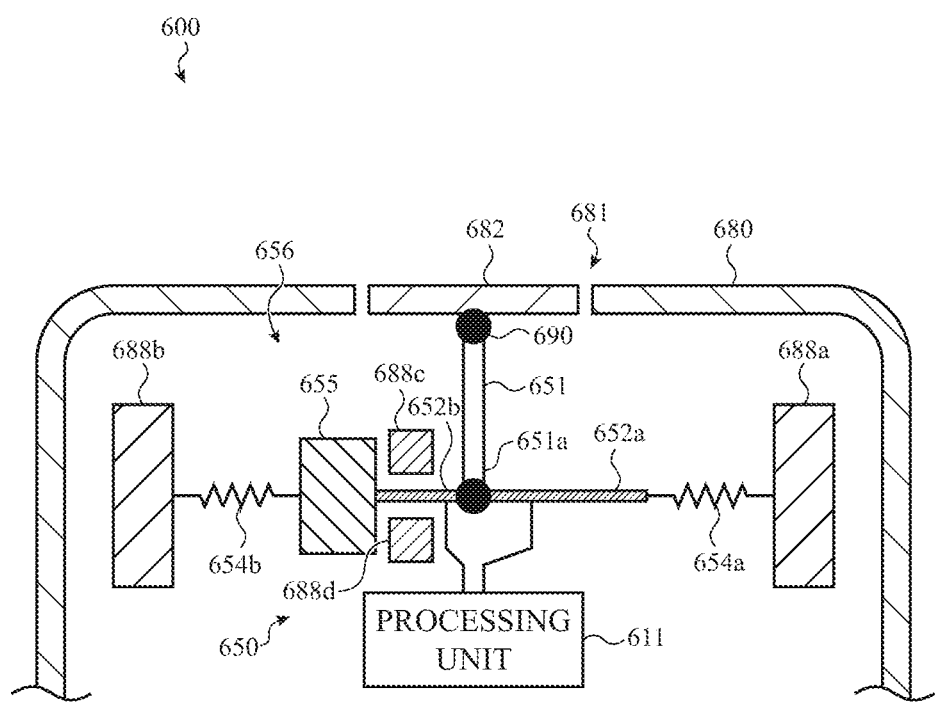
Figure 6E:
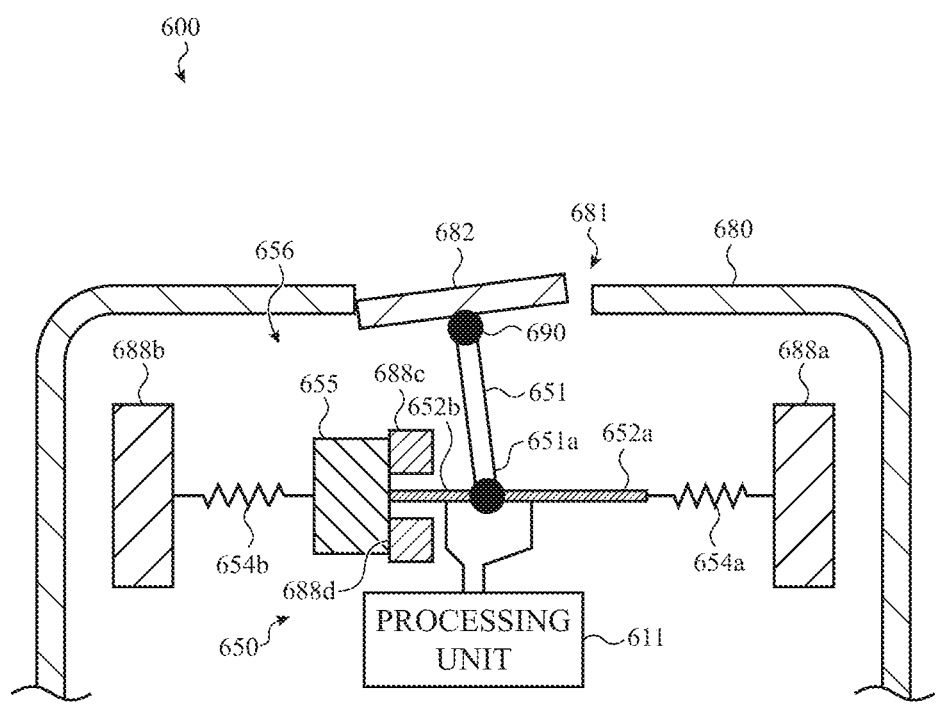
Figure 6F:
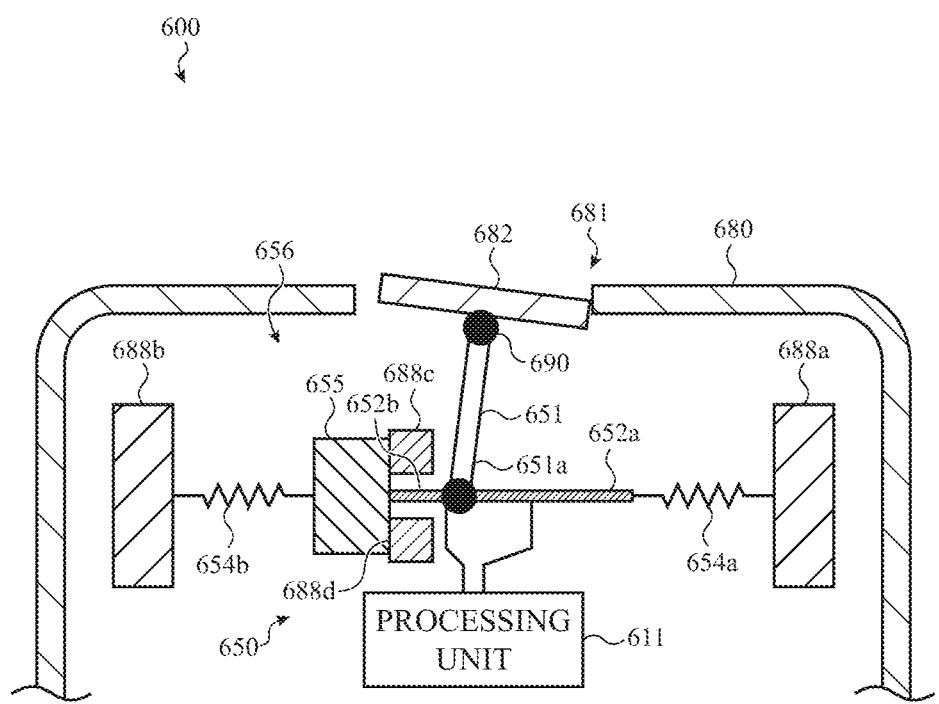

FIGS. 6A-6C show the contact member 682 translating or oscillating laterally, but in various embodiments, the haptic device 650 may cause the contact member 682 to move in other ways to produce a vibration or tactile effect along the external surface of the electronic device 600, including rotating, rocking, or translating or oscillating in other directions. As shown in FIGS. 6D-6F, the haptic device 650 may cause the contact member to pivot or rock relative to the housing member 680.

Turning to FIG. 6D, the contact member 682 and/or the connector 651 may be attached to a pivot point 690 about which the contact member and/or the connector rotate. As shown in FIG. 6E, as the SMA actuation member 652a contracts, the lower end 651a of the connector 651 moves to the right, which causes the connector 651 and the contact member 682 to pivot around the pivot point 690 in a counter-clockwise direction, thereby causing the contact member 682 to rock in a leftward direction. As shown in FIG. 6F, as the SMA actuation member 652b contracts, the bottom end 651a of the connector 651 moves to the left, which causes the connector 651 and the contact member 682 to pivot around the pivot point 690 in a clockwise direction, thereby causing the contact member 682 to rock in a rightward direction.

As discussed above with respect to FIGS. 6A-6C, contraction and elongation of the SMA actuation members may be repeated to repeatedly rock or pivot the contact member 682 in alternating directions (e.g., left to right and right to left with respect to FIGS. 6A-6C) to produce one or more haptic outputs and/or portions thereof.

In some cases, either of the spring 654 or the SMA actuation member 652b may be omitted from the restoration mechanism 656. The directions of movement described with respect to FIGS. 6A-6F are examples for illustrative purposes only. In various embodiments, the directions of movement may be different from those described.

Figure 7A:
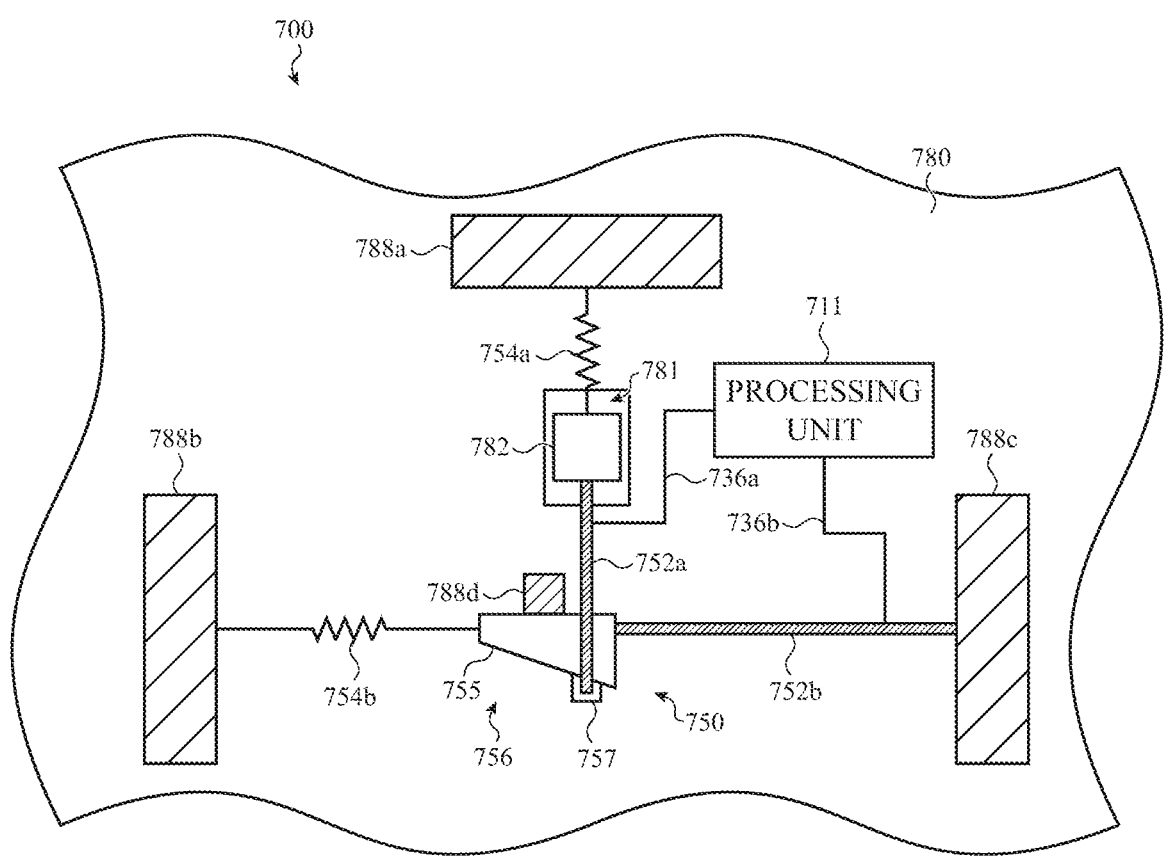
FIGS. 7A-7C show functional block diagrams of an example haptic device having an SMA actuation member and a restoration mechanism installed in an example electronic device.
Figure 7B:
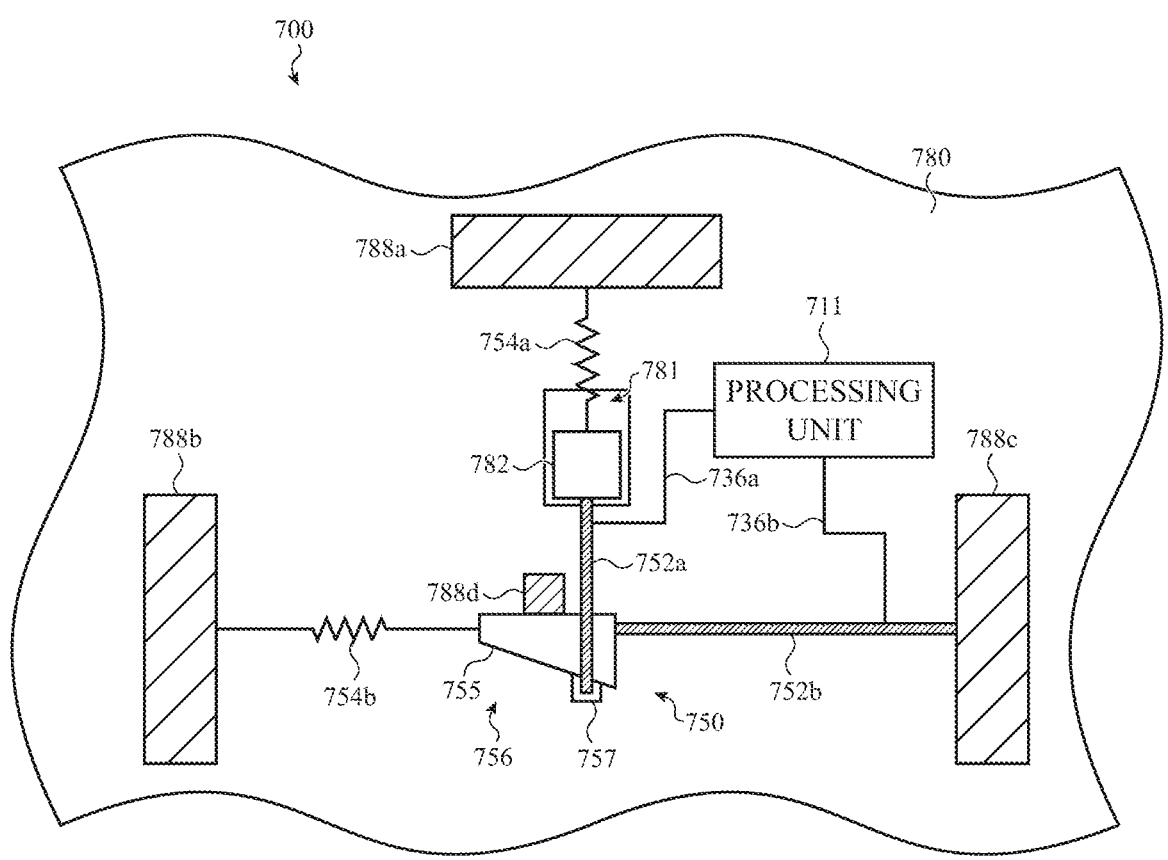
Figure 7C:
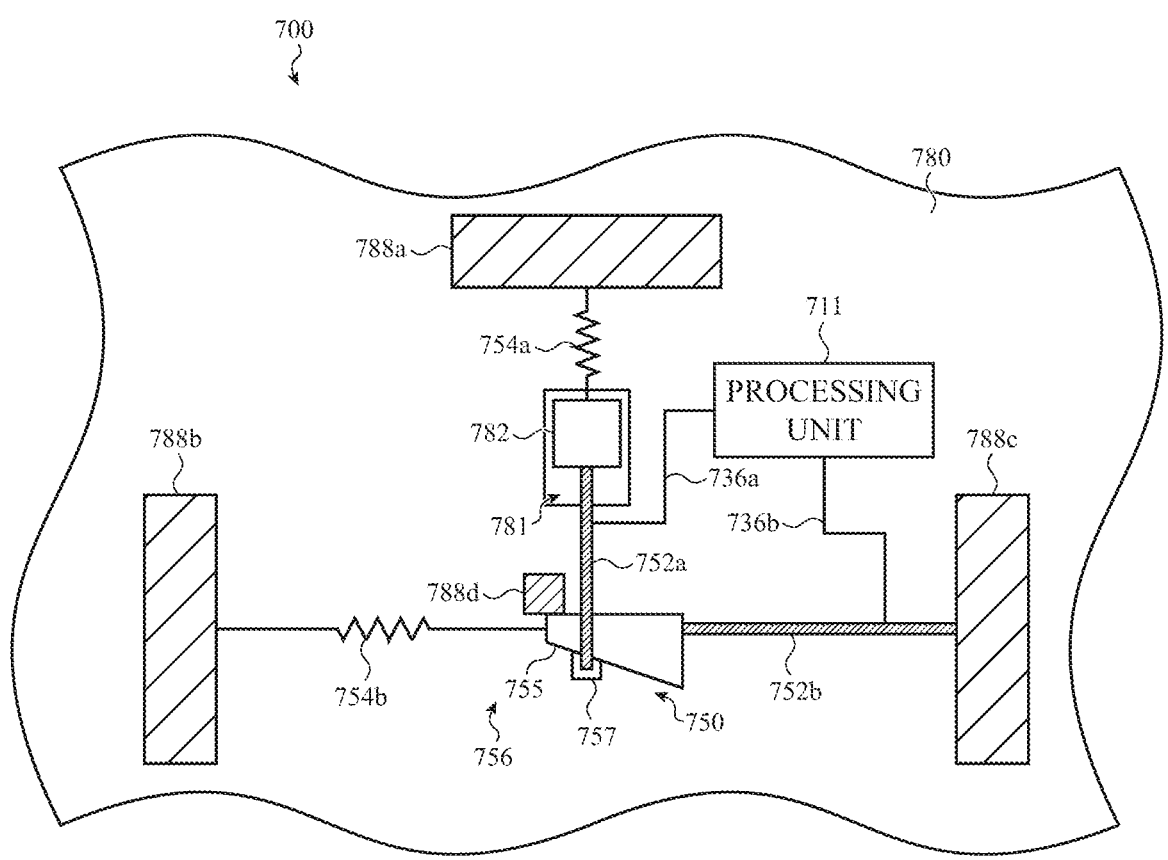

FIGS. 7A-7C show functional block diagrams of an example haptic device having an SMA actuation member 752a and a restoration mechanism 756, installed in an example electronic device 700. The example electronic device 700 of FIGS. 7A-7C may have similar structure, components, and functionality as other electronic devices discussed herein. FIG. 7A illustrates a contact member 782 positioned in an opening 781 of a housing member 780. In some cases, the haptic device 750 causes the contact member 782 to translate or oscillate laterally (e.g., up and down with respect to FIG. 7A) relative to the housing member 780. In some cases, the lateral translation or oscillation is along a path that is parallel to an external surface of the electronic device (e.g., the front external surface or the rear external surface). The translation or oscillation may produce a vibration or tactile effect along the external surface of the electronic device 700.

In some cases, the haptic device 750 includes an SMA actuation member 752a and a restoration mechanism 756. A first end of the SMA actuation member 752a may be coupled to the contact member 782, and a second end of the SMA actuation member 752a may be engaged with a block member 755 of the restoration mechanism 756. For example, a support member 788d may constrain upward movement of the block member 755, and an engagement member 757 may retain the SMA actuation member 752a to the block member while allowing the block member to slide (e.g., left and right) with respect to the engagement member and the SMA actuation member. In some cases the contact member 782 is coupled to a support member 788a. In some cases, a spring 754a couples the contact member 782 to the support member 788a. The spring 754a may be coupled to the contact member 782 on a first side, and the SMA actuation member 752a may be coupled to the contact member on a second, opposite side.

In some cases, the SMA actuation member 752a contracts from a first shape having a first length to a second shape having a second, shorter length in response to a signal received from the processing unit 711, and, after the contraction, the spring 754a elongates the SMA actuation member 752a to the first shape or a similar shape (e.g., a third shape having a length between the length of the first shape and the length of the second shape).

FIG. 7A shows the contact member 782 in a first position. In some cases, the first position is a default position of the contact member 782. The contact member 782 may be flush with the external surface of the housing member 780, or it may be recessed or protruding relative to the external surface.

In some cases, the SMA actuation member 752a is responsive to a signal from the processing unit 711, which causes a current to be applied to the SMA actuation member 752a, thereby causing the SMA actuation member 752a to contract. As shown in FIG. 7B, contraction of the SMA actuation member 752a may cause the contact member 782 to translate downward from the first position shown in FIG. 7A to a second position shown in FIG. 7B. The spring 754a may expand to allow the movement of the contact member 782 to the second position as shown in FIG. 7B. The downward translation of the contact member 782 may produce a first portion of a haptic output.

The restoration mechanism 756 may include the block member 755 positioned between and coupled to a second spring 754b and a second SMA actuation member 752b. The second spring 754b may be coupled to a support member 788b, and the second SMA actuation member 752b may be coupled to a support member 788c. The SMA actuation members 752a and 752b may be electrically coupled to a processing unit 711 (e.g., by connectors 736a and 736b) and configured to contract in response to receiving signals from the processing unit 711.

In the present example and in many of the examples described herein, the restoration mechanism 756 may include a spring 754b, a spring 754b and an additional SMA actuation member, or an additional SMA actuation member without a spring 754b. As discussed previously, the spring 754b may be omitted and the restoration mechanism 756 may rely primarily on the additional SMA actuation member to provide a restoration force to the (second) SMA actuation member 752b. Similar to the second SMA actuation member 752b, the additional SMA actuation member of the restoration mechanism 756 may be responsive to a signal produced by the processing unit 711, which causes a drive current or other electrical signal to alter a shape and/or length of the second SMA actuation member.

As noted above, in many cases, the time required for elongation of the SMA actuation member 752a is sufficiently long that it limits the number of successive contractions and elongations that can occur in a given time period. In some cases, the spring 754a elongates the SMA actuation member 752a after the contraction to prepare the SMA actuation member 752a for a subsequent contraction.

Following the application of the current to the SMA actuation member 752a, the applied current is ceased, which allows the SMA actuation member 752a to begin elongating back to the first shape or a similar shape. At this point, the spring 754a may also begin to contract, which exerts a tensile force on the SMA actuation member 752a. The tensile force(s) may accelerate the elongation of the SMA actuation member 752a, causing the SMA actuation member 752a to elongate faster and/or more completely than if no tensile force was applied.

As the spring 754a elongates the SMA actuation member 752a, the contact member 782 may move upward with respect to FIG. 7B. In some cases, an additional signal is applied to the second SMA actuation member 752b, causing the second SMA actuation member to contract. This may cause the spring 754b to expand and the block member 755 to move rightward with respect to FIG. 7B, which allows the engagement member 757 to slide along a sloped surface of the block member 755, thereby allowing the contact member 782 to move upward.

In some cases, the upward translation of the contact member 782 may produce a second portion of the haptic output. In some cases, the restoration mechanism 756 and/or the spring 754a return the contact member 782 to the first position shown in FIG. 7A. In other cases, the restoration mechanism 756 and/or the spring 754a may move the contact member 782 to a third position above the first position, as shown in FIG. 7C.

In various embodiments, once the SMA actuation member 752a has been elongated (either partially or fully), it may be subsequently contracted in response to receiving another signal from the processing unit 711 and subsequently elongated by the restoration mechanism 758. Contraction and elongation may be repeated to repeatedly move the contact member 782 in alternating directions (e.g., up and down with respect to FIGS. 7A-7C) to produce one or more haptic outputs and/or portions thereof.

In various embodiments, a compliant member may be disposed between the contact member 782 and the housing member 780. The compliant member may form a seal between the contact member 782 and the housing member 780 to exclude contaminants from the interior of the electronic device, while still allowing the contact member 782 to move relative to the housing member 780 to produce a haptic output.

In some cases, either of the spring 754b or the SMA actuation member 752b may be omitted from the restoration mechanism 756. The directions of movement described with respect to FIGS. 7A-7C are examples for illustrative purposes only. In various embodiments, the directions of movement may be different from those described.

Figure 8A:
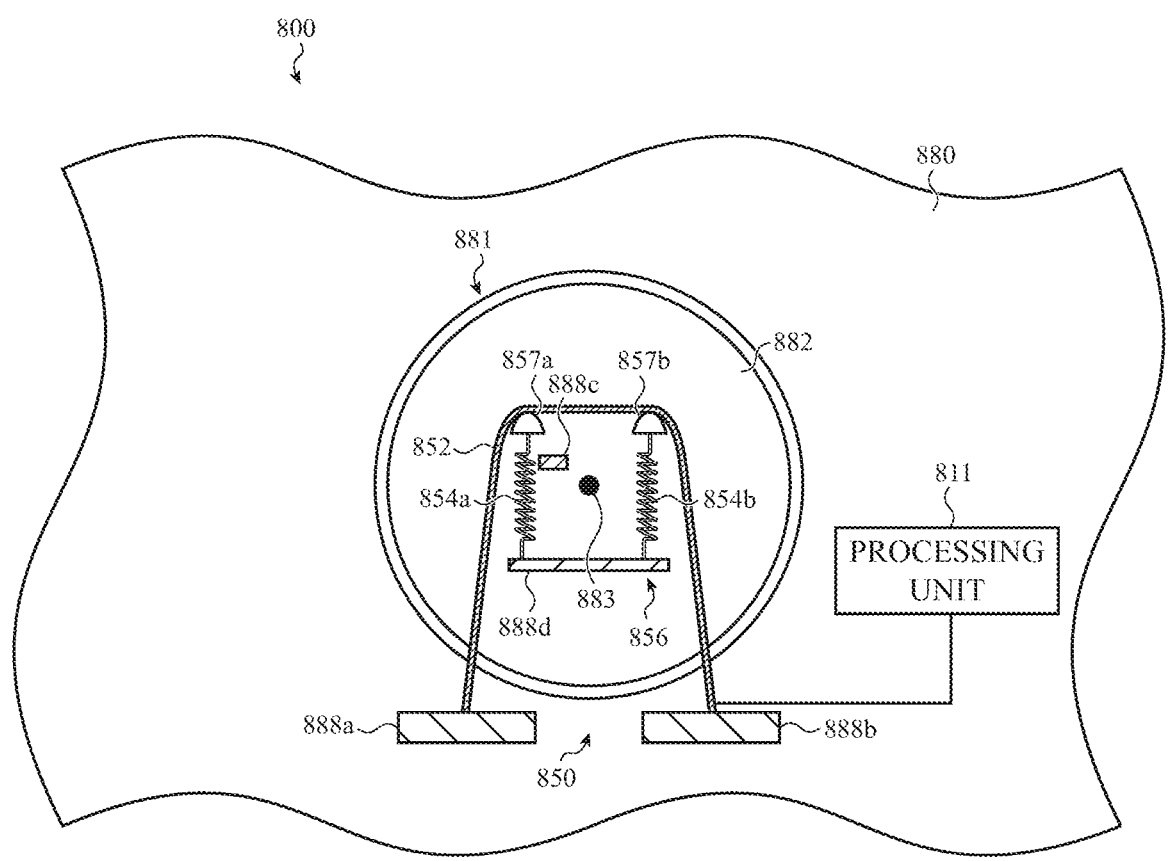
FIGS. 8A-8C show functional block diagrams of an example haptic device having an SMA actuation member and a restoration mechanism installed in an example electronic device.
Figure 8B:
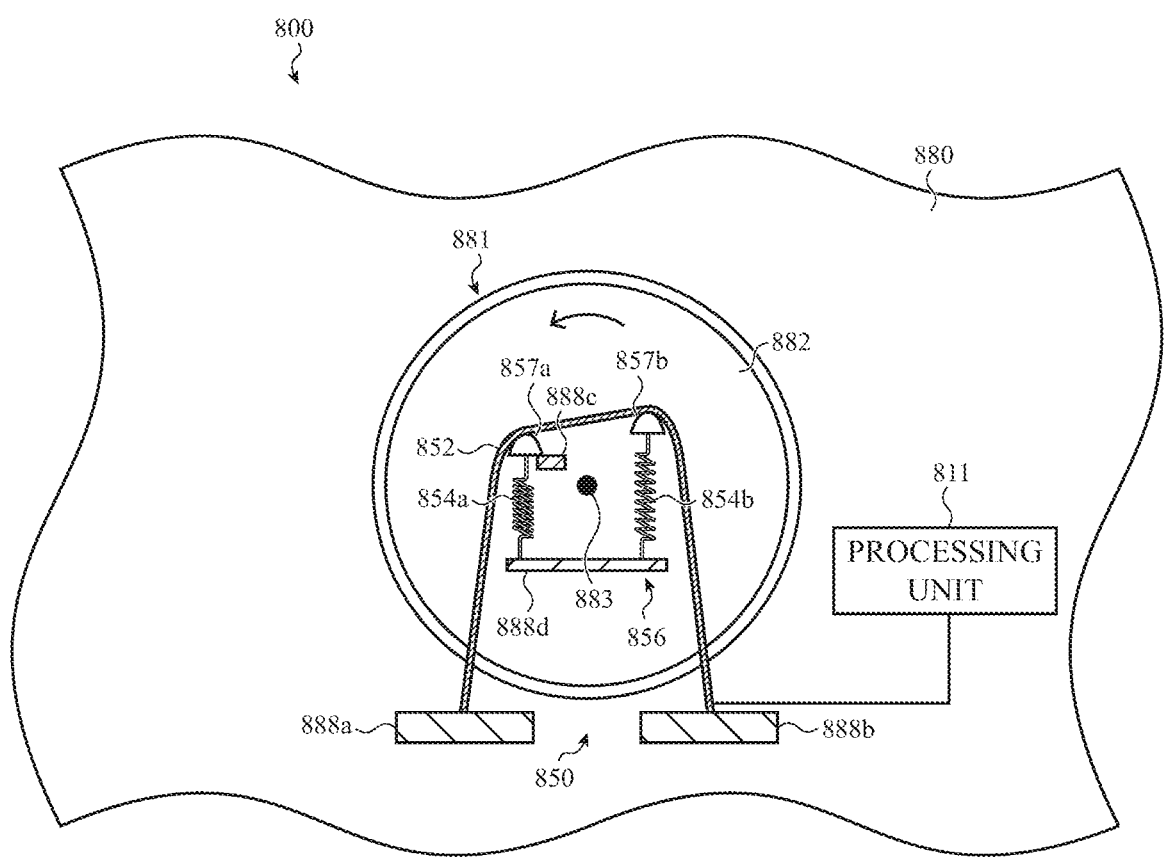
Figure 8C:
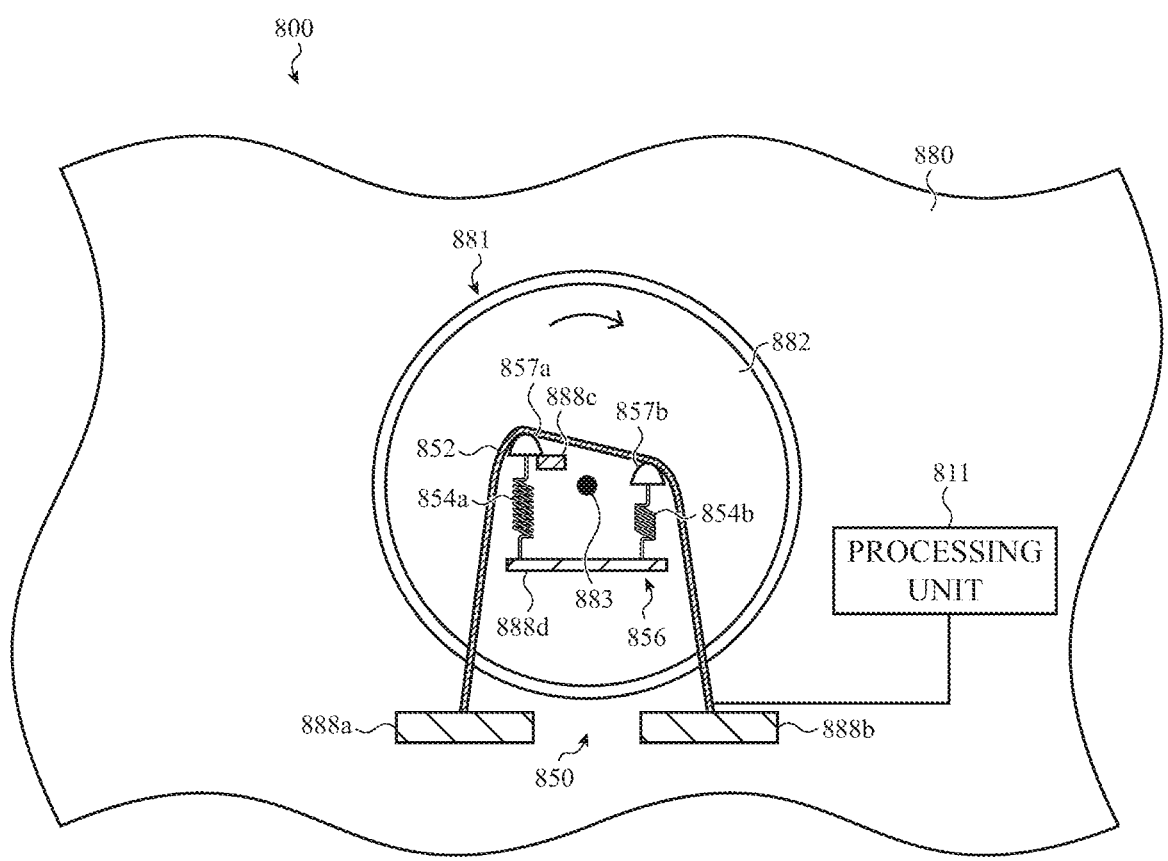

FIGS. 8A-8C show functional block diagrams of an example haptic device having an SMA actuation member 852 and a restoration mechanism 856, installed in an example electronic device 800. The example electronic device 800 of FIGS. 8A-8C may have similar structure, components, and functionality as other electronic devices discussed herein. FIG. 8A illustrates a contact member 882 positioned in an opening 881 of a housing member 880. In some cases, the haptic device 850 causes the contact member 882 to rotate (e.g., clockwise and counter-clockwise with respect to FIG. 8A) with respect to the housing member 880 to provide a haptic output. In some cases, the contact member 882 rotates around an axle 883 that is fixed with respect to the housing member 880. The rotation may produce a vibration or tactile effect along the external surface of the electronic device 800.

In some cases, the haptic device 850 includes an SMA actuation member 852 and a restoration mechanism 856. A first end of the SMA actuation member 852 may be coupled to a support member 888*a*, and a second end of the SMA actuation member 852 may be coupled to a support member 888*b*. In some cases, the SMA actuation member 852 contracts from a first shape having a first length to a second shape having a second, shorter length in response to a signal received from the processing unit 811, and, after the contraction, the restoration mechanism 856 may elongate the SMA actuation member 852 to the first shape or a similar shape (e.g., a third shape having a length between the length of the first shape and the length of the second shape).

The restoration mechanism 856 may include block members 857*a* and 857*b* and springs 854*a* and 854*b*. The SMA actuation member 852*a* may extend partially around and contact the block members 857*a* and 857*b*, which are coupled by the springs 854*a* and 854*b* to a support member 888*d*. FIG. 8A shows the contact member 882 in a first position. In some cases, the first position is a default position of the contact member 882.

In some cases, the SMA actuation member 852 is responsive to a signal produced by the processing unit 811, causing a current to be applied to the SMA actuation member 852, thereby causing the SMA actuation member 852 to contract. In some cases, a spring constant of the spring 854*a* is much lower than a spring constant of the spring 854*b*, so contraction of the SMA actuation member 852 causes the spring 854*a* to compress significantly more than the spring 854*b*. As shown in FIG. 8B, contraction of the SMA actuation member 852 and the resulting compression of the spring 854*a* causes the contact member 882 to rotate counter-clockwise from the first position shown in FIG. 8A to a second position shown in FIG. 8B. The counter-clockwise rotation of the contact member 882 may produce a first portion of a haptic output.

The spring 854*a* may continue to compress until it reaches a support member 888*c*, which stops movement of the block member 857. At this point, contraction of the SMA actuation member 852 begins to compress the spring 854*b*. As shown in FIG. 8C, contraction of the SMA actuation member 852 and the resulting compression of the spring 854*b* causes the contact member 882 to rotate clockwise. In some cases, the clockwise rotation of the contact member 882 may produce a second portion of the haptic output. In some cases, the clockwise rotation returns the contact member 882 to the first position shown in FIG. 8A. In other cases, the clockwise rotation may rotate the contact member 882 to a third position, as shown in FIG. 8C.

As noted above, in many cases, the time required for elongation of the SMA actuation member 852 is sufficiently long that it limits the number of successive contractions and elongations that can occur in a given time period. In some cases, the restoration mechanism 856 elongates the SMA actuation member 852 after the contraction to prepare the SMA actuation member 852 for a subsequent contraction. Following the application of the current to the SMA actuation member 852, the applied current is ceased, which allows the SMA actuation member to begin elongating back to the first shape or a similar shape.

At this point, the springs 854*a* and 854*b* may exert tensile forces on the SMA actuation member 852. The tensile force(s) may accelerate the elongation of the SMA actuation member 852, causing the SMA actuation member to elongate faster and/or more completely than if no tensile force was applied.

In various embodiments, once the SMA actuation member 852 has been elongated (either partially or fully), it may be subsequently contracted in response to receiving another signal from the processing unit 811 and subsequently elongated by the restoration mechanism 856. Contraction and elongation may be repeated to repeatedly move the contact member 882 in alternating directions (e.g., clockwise and counter-clockwise) to produce one or more haptic outputs and/or portions thereof.

In various embodiments, a compliant member may be disposed between the contact member 882 and the housing member 880. The compliant member may form a seal between the contact member 882 and the housing member 880 to exclude contaminants from the interior of the electronic device, while still allowing the contact member 882 to move relative to the housing member 880 to produce a haptic output.

The directions of movement described with respect to FIGS. 8A-8C are examples for illustrative purposes only. In various embodiments, the directions of movement may be different from those described.

Figure 9A:
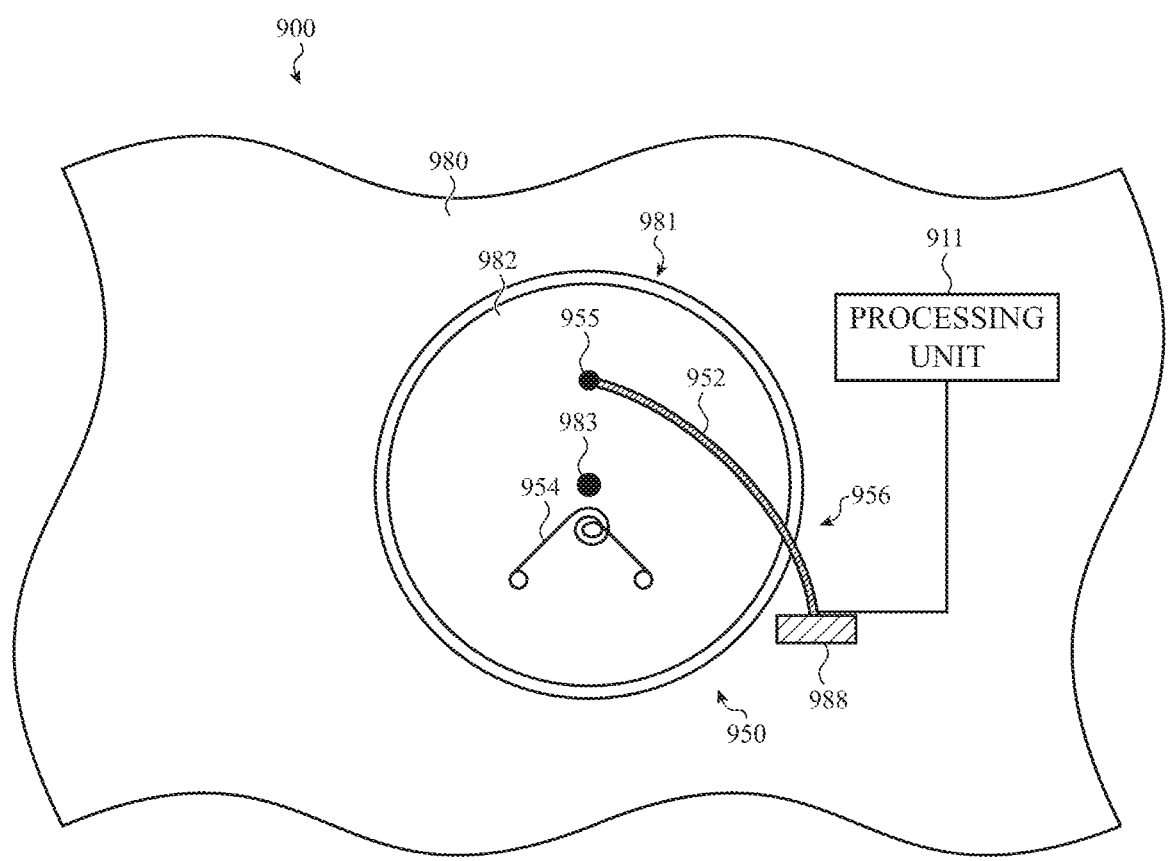
FIGS. 9A-9B show functional block diagrams of an example haptic device having an SMA actuation member and a restoration mechanism installed in an example electronic device.
Figure 9B:
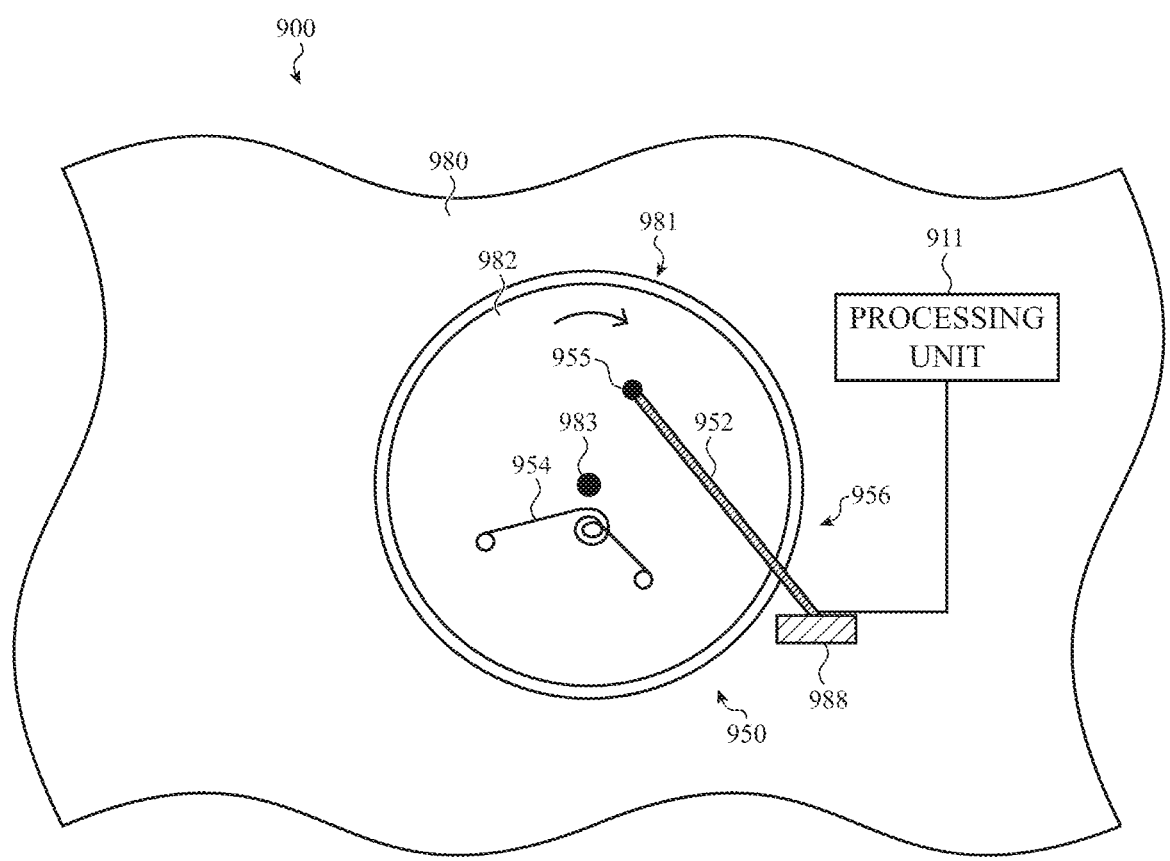

FIGS. 9A-9B show functional block diagrams of an example haptic device having an SMA actuation member 952 and a restoration mechanism 956, installed in an example electronic device 900. The example electronic device 900 of FIGS. 9A-9B may have similar structure, components, and functionality as other electronic devices discussed herein. FIG. 8A illustrates a contact member 982 positioned in an opening 981 of a housing member 980. In some cases, the haptic device 950 causes the contact member 982 to rotate (e.g., clockwise and counter-clockwise with respect to FIG. 9A) with respect to the housing member 980 to provide a haptic output. In some cases, the contact member 982 rotates around an axle 983 that is fixed with respect to the housing member 980. The rotation may produce a vibration or tactile effect along the external surface of the electronic device 900.

In some cases, the haptic device 950 includes an SMA actuation member 952 and a restoration mechanism 956. A first end of the SMA actuation member 952 may be coupled to a support member 988, and a second end of the SMA actuation member may be coupled to a connection point 955 of the contact member 982. In some cases, the SMA actuation member 952 contracts from a first shape having a first length to a second shape having a second, shorter length in response to a signal received from the processing unit 911, and, after the contraction, the restoration mechanism 956 may elongate the SMA actuation member 952 to the first shape or a similar shape (e.g., a third shape having a length between the length of the first shape and the length of the second shape). FIG. 9A shows the contact member 982 in a first position. In some cases, the first position is a default position of the contact member 982.

In some cases, the SMA actuation member 952 is responsive to a signal from the processing unit 911, causing a current to be applied to the SMA actuation member 952, thereby causing the SMA actuation member 952 to contract. As shown in FIG. 9B, contraction of the SMA actuation member 952 may cause the contact member 982 to rotate clockwise from the first position shown in FIG. 9A to a second position shown in FIG. 9B. The clockwise rotation of the contact member 982 may produce a first portion of a haptic output.

As noted above, in many cases, the time required for elongation of the SMA actuation member 952 is sufficiently long that it limits the number of successive contractions and elongations that can occur in a given time period. In some cases, the restoration mechanism 956 elongates the SMA actuation member 952 after the contraction to prepare the SMA actuation member for a subsequent contraction. Following the application of the current to the SMA actuation member 952, the applied current is ceased, which allows the SMA actuation member to begin elongating back to the first shape or a similar shape.

As the contact member 982 rotates clockwise in response to the contraction of the SMA actuation member 952, a torsion spring 954 of the restoration mechanism 956 may be rotated. As the SMA actuation member 952 begins to elongate, the torsion spring 954 may unwind and exert a counter-clockwise torque on the contact member 982, thereby exerting a tensile force on the SMA actuation member 952. The tensile force may accelerate the elongation of the SMA actuation member 952, causing the SMA actuation member to elongate faster and/or more completely than if no tensile force was applied.

As the restoration mechanism 956 elongates the SMA actuation member 952, the contact member 982 may rotate counter-clockwise. In some cases, the counter-clockwise rotation of the contact member 982 may produce a second portion of the haptic output. In some cases, the restoration mechanism 956 returns the contact member 982 to the first position shown in FIG. 9A.

In various embodiments, once the SMA actuation member 952 has been elongated (either partially or fully), it may be subsequently contracted in response to receiving another signal from the processing unit 911 and subsequently elongated by the restoration mechanism 956. Contraction and elongation may be repeated to repeatedly move the contact member 982 in alternating directions (e.g., clockwise and counter-clockwise) to produce one or more haptic outputs and/or portions thereof.

In various embodiments, a compliant member may be disposed between the contact member 982 and the housing member 980. The compliant member may form a seal between the contact member 982 and the housing member 980 to exclude contaminants from the interior of the electronic device, while still allowing the contact member 982 to move relative to the housing member 980 to produce a haptic output.

The directions of movement described with respect to FIGS. 9A-9B are examples for illustrative purposes only. In various embodiments, the directions of movement may be different from those described.

Figure 10A:
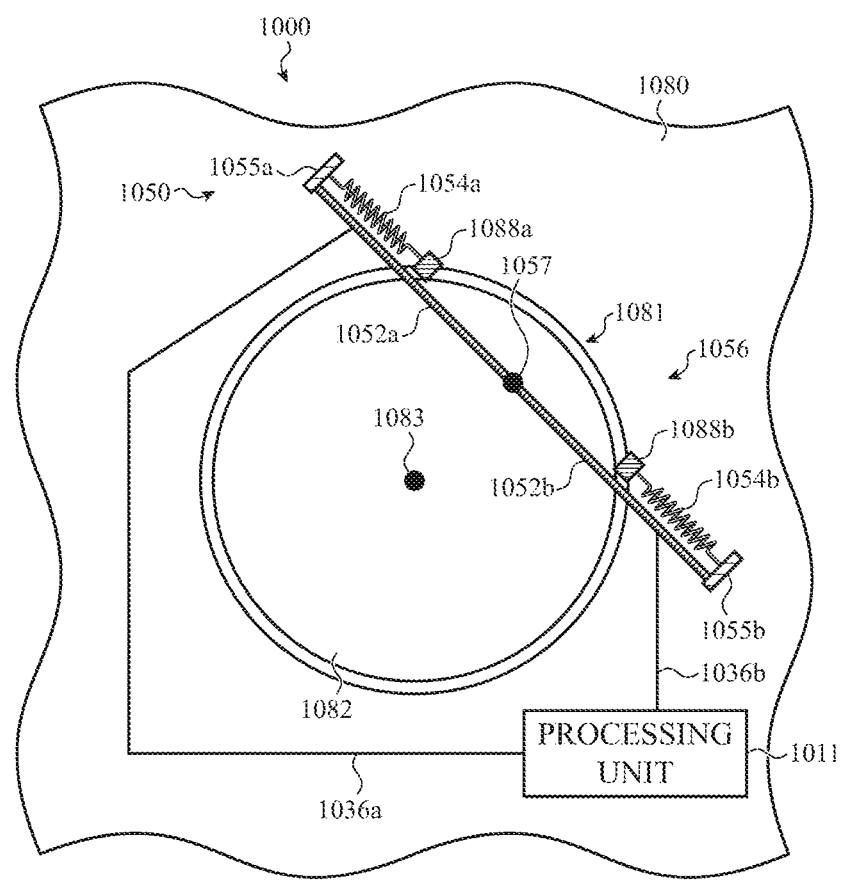
FIGS. 10A-10C show functional block diagrams of an example haptic device having an SMA actuation member and a restoration mechanism installed in an example electronic device.
Figure 10B:
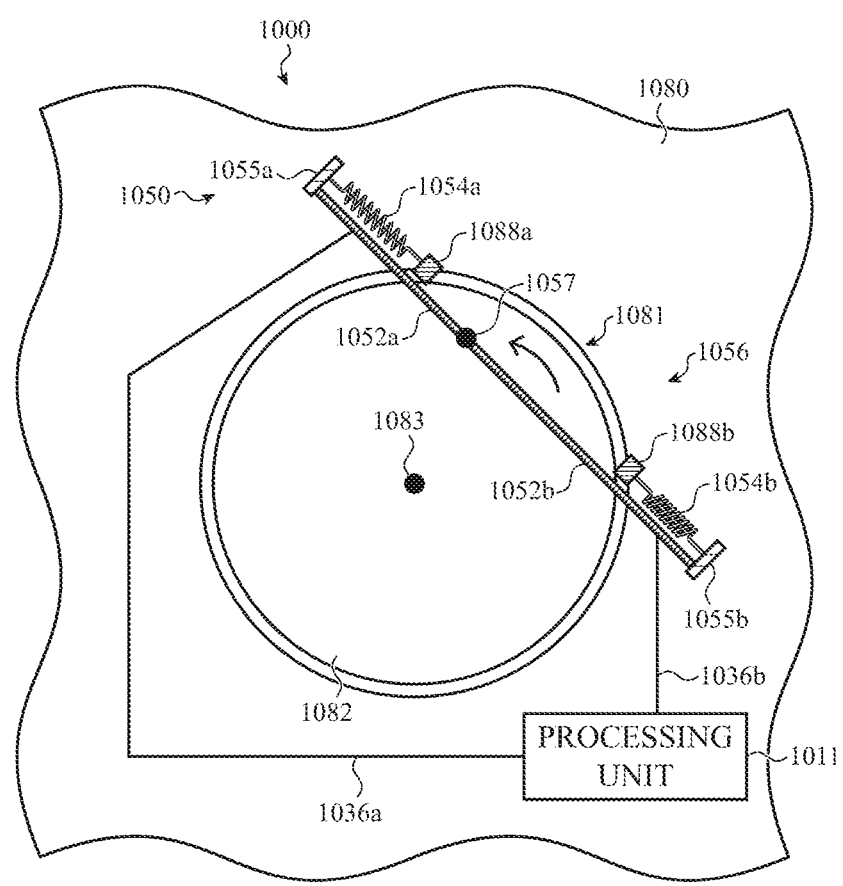
Figure 10C:
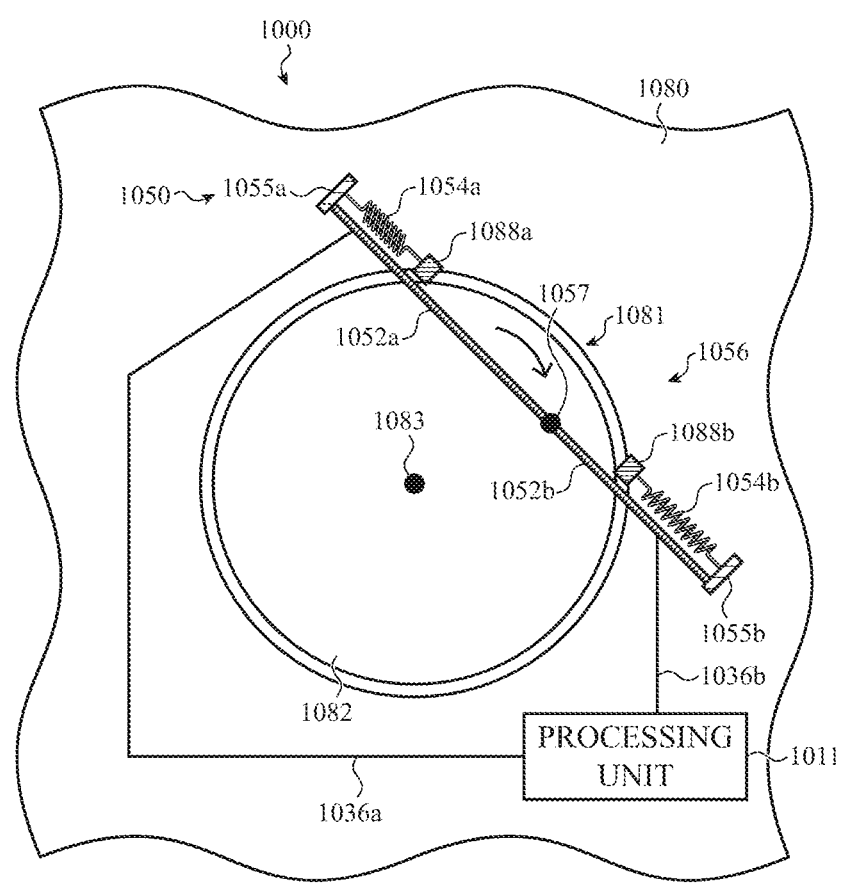

FIGS. 10A-10C show functional block diagrams of an example haptic device 1050 having an SMA actuation member 1052a and a restoration mechanism 1056, installed in an example electronic device 1000. The example electronic device 1000 of FIGS. 10A-10C may have similar structure, components, and functionality as other electronic devices discussed herein. FIG. 10A illustrates a contact member 1082 positioned in an opening 1081 of a housing member 1080. In some cases, the haptic device 1050 causes the contact member 1082 to rotate (e.g., clockwise and counter-clockwise with respect to FIG. 10A) with respect to the housing member 1080 to provide a haptic output. In some cases, the contact member 1082 rotates around an axle 1083 that is fixed with respect to the housing member 1080. The rotation may produce a vibration or tactile effect along the external surface of the electronic device 1000.

In some cases, the haptic device 1050 includes an SMA actuation member 1052a and a restoration mechanism 1056. The SMA actuation member 1052a and the restoration mechanism 1056 may couple the contact member 1082 to other components of the electronic device. In some cases, a first end of the SMA actuation member 1052 is coupled to a support member 1088a via a spring 1054a and a block member 1055a, and a second end is coupled to a connection point 1057 of the contact member 1082. In some cases, a first end of the restoration mechanism 1056 is coupled to a support member 1088b, and a second end is coupled to the connection point 1057 of the contact member 1082. The support members 1088a and 1088b may be portions of the housing member 1080 or may be attached to the housing member 1080 or another component of the electronic device.

In some cases, the SMA actuation member 1052a contracts from a first shape having a first length to a second shape having a second, shorter length in response to a signal received from the processing unit 1011, and, after the contraction, the restoration mechanism 1056 elongates the SMA actuation member 1052 to the first shape or a similar shape (e.g., a third shape having a length between the length of the first shape and the length of the second shape). FIG. 10A shows the contact member 1082 in a first position. In some cases, the first position is a default position of the contact member 1082.

In some cases, the SMA actuation member 1052a is responsive to a signal from the processing unit 1011, causing a current to be applied to the SMA actuation member 1052a, thereby causing the SMA actuation member 1052a to contract. As shown in FIG. 10B, contraction of the SMA actuation member 1052a may cause the contact member 1082 to rotate counter-clockwise from the first position shown in FIG. 10A to a second position shown in FIG. 10B. The contraction of the SMA actuation member 1052a may cause the spring 1054a to compress. The counter-clockwise rotation of the contact member 1082 may produce a first portion of a haptic output.

The restoration mechanism 1056 may include a second SMA actuation member 1052b, a second block member 1055b, and a second spring 1054b. The SMA actuation members 1052a and 1052b may be electrically coupled to a processing unit 1011 (e.g., by connectors 1036a and 1036b) and configured to contract in response to receiving signals from the processing unit 1011.

As noted above, in many cases, the time required for elongation of the SMA actuation member 1052a is sufficiently long that it limits the number of successive contractions and elongations that can occur in a given time period. In some cases, the restoration mechanism 1056 elongates the SMA actuation member 1052a after the contraction to prepare the SMA actuation member 1052a for a subsequent contraction. Following the application of the current to the SMA actuation member 1052a, the applied current is ceased, which allows the SMA actuation member to begin elongating back to the first shape or a similar shape.

At this point, the spring 1054a may also begin to expand, which exerts a tensile force on the SMA actuation member 1052a. In some cases, an additional signal is applied to the second SMA actuation member 1052b, causing the second SMA actuation member to contract, which exerts an additional tensile force on the first SMA actuation member 1052a. The tensile force(s) may accelerate the elongation of the SMA actuation member 1052a, causing the SMA actuation member 1052a to elongate faster and/or more completely than if no tensile force was applied.

As the restoration mechanism 1056 elongates the SMA actuation member 1052a, the contact member 1082 may rotate clockwise. In some cases, the clockwise rotation of the contact member 1082 may produce a second portion of the haptic output. In some cases, the restoration mechanism 1056 returns the contact member 1082 to the first position shown in FIG. 10A. In other cases, the restoration mechanism 1056 may rotate the contact member 1082 to a third position, as shown in FIG. 10C.

In various embodiments, once the SMA actuation member 1052*a* has been elongated (either partially or fully), it may be subsequently contracted in response to receiving another signal from the processing unit 1011 and subsequently elongated by the restoration mechanism 1056. Contraction and elongation may be repeated to repeatedly move the contact member 1082 in alternating directions (e.g., clockwise and counter-clockwise) to produce one or more haptic outputs and/or portions thereof.

In various embodiments, a compliant member may be disposed between the contact member 1082 and the housing member 1080. The compliant member may form a seal between the contact member 1082 and the housing member 1080 to exclude contaminants from the interior of the electronic device, while still allowing the contact member 1082 to move relative to the housing member 1080 to produce a haptic output.

The directions of movement described with respect to FIGS. 10A-10C are examples for illustrative purposes only. In various embodiments, the directions of movement may be different from those described.

In various embodiments, the haptic devices described herein (e.g., haptic devices 150, 350, 450, 650, 750, 850, 950, and 1050) may be used to provide localized and/or global haptic outputs along an external surface of an electronic device. In some cases, the haptic devices described herein may move (e.g., rotate, translate, oscillate, or vibrate) the contact members described with respect to FIGS. 1-10C may provide localized haptic outputs by producing a vibration or tactile effect along a portion of an external surface of an electronic device. In some cases, the haptic devices described herein may provide a global haptic output by moving a mass or weighted member within the enclosure. For example, the contact member of any of the electronic devices described herein may be a mass or weighted member positioned within a device enclosure instead of defining an external surface of the device. The haptic devices described herein may cause the mass or weighted member to move and, in some cases, oscillate, to produce a perceptible vibration or tactile effect along an external surface of the electronic device.

Figure 11:
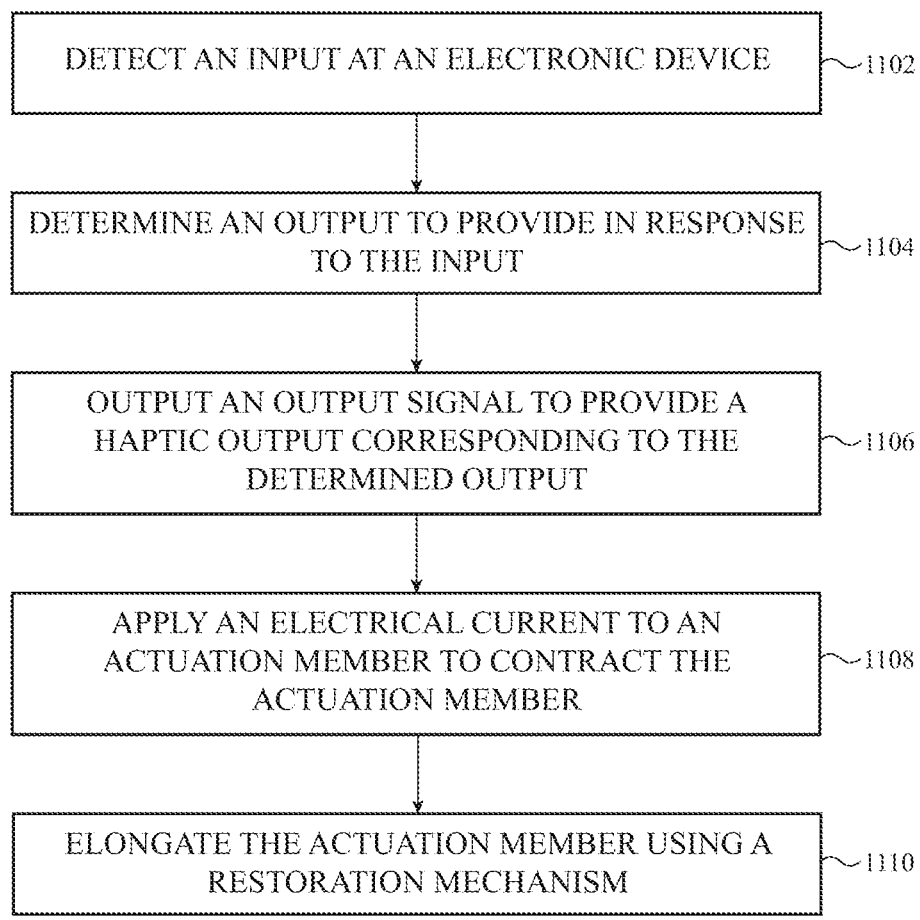
FIG. 11 shows an example method for providing haptic feedback using a haptic device with an actuation member formed from a shape-memory alloy material.

FIG. 11 shows an example method 1100 for providing haptic feedback using a haptic device with an actuation member formed from a shape-memory alloy material. At block 1102, the electronic watch detects an input at the electronic device. For example, the input may be a rotational input at a crown detected by sensing rotational movement of the crown. As another example, the input may be a touch input detected along a touch-sensitive display. As still another example, detecting the input may include determining an electrocardiogram using one or more voltages detected at the electronic device. In some cases, the processing unit may determine whether the input exceeds a threshold level of movement (e.g., a threshold level of rotational movement, a threshold level of translation, etc.). In some cases, the method only proceeds if the input exceeds the threshold level of movement.

At block 1104, the processing unit determines an output to be produced by the electronic device in response to the input received at block 1102. In some cases, the output is determined in response to detecting the input at block 1102. In some cases, the output corresponds to one or more characteristics of the input detected at block 1102. For example, the output may correspond to a rotational speed or position of the crown, an output associated with a rotational input, a user interface command associated with the user input, or the like. The processing unit may determine one or more characteristics of the input.

At block 1106, the processing unit outputs an output signal to provide a haptic output that corresponds to the output determined at block 1104. The output signal may be transmitted to a haptic device of the electronic device to direct the haptic device to produce the haptic output.

In some cases, determining the output at block 1104 may include determining a strength, length, or other characteristics of a haptic output to be produced. For example, the processing unit may determine whether to provide a localized haptic output or a global haptic output based, at least in part, on a characteristic of the input.

At block 1108, in response to receiving the output signal from the processing unit, the haptic device applies a current or other electrical signal to an SMA actuation member to contract the SMA actuation member. In some cases, contraction of the SMA actuation member produces a first portion of the haptic output.

At block 1110, in response to contracting the SMA actuation member, the haptic device elongates the SMA actuation member using a restoration mechanism. In some cases, elongation of the SMA actuation member produces a second portion of the haptic output. As noted above, in some cases, elongating the SMA actuation member includes applying a tensile force to the SMA actuation member using the restoration mechanism.

In some cases, the elongation of the SMA actuation member may prepare the SMA actuation member for a subsequent contraction. In various embodiments, once the SMA actuation member has been elongated (either partially or fully), it may be subsequently contracted by applying an additional electrical current to the SMA actuation member (e.g., in response to receiving another output signal from the processing unit) to provide a third portion of the haptic output. The SMA actuation member may be subsequently elongated by the restoration mechanism, which may provide a fourth portion of the haptic output. Contraction and elongation may be repeated to repeatedly move the contact member in alternating directions to produce one or more haptic outputs and/or portions thereof.

In some cases, a first portion of a haptic output may be provided by causing the SMA actuation member to contract less than a total contraction amount and a second portion of a haptic output may be provided by causing the SMA actuation member to contract an additional amount.

The method 1100 is an example method for providing haptic outputs and is not meant to be limiting. Methods for providing haptic outputs may omit and/or add steps to the method 1100. Similarly, steps of the method 1100 may be performed in different orders than the example order discussed above.

Figure 12:
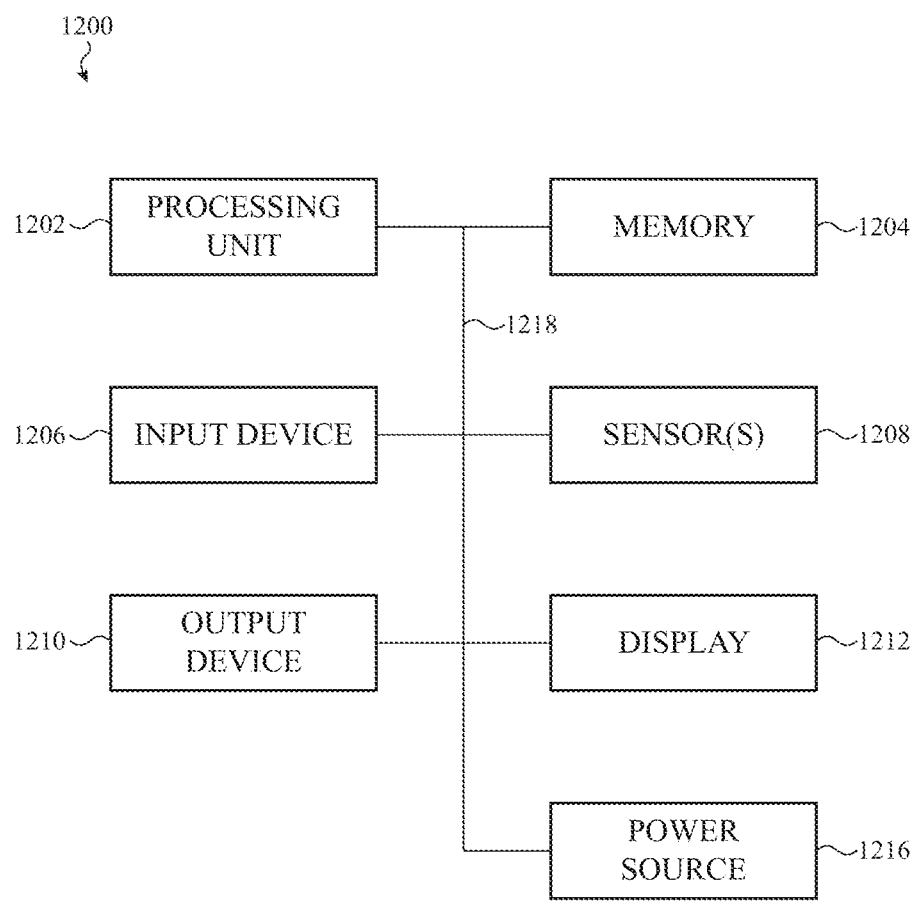
FIG. 12 shows a sample electrical block diagram of an electronic device that may incorporate a haptic device, as described herein.

FIG. 12 shows a sample electrical block diagram of an electronic device 1200 that may incorporate a haptic device having an SMA actuation member and a restoration mechanism. The electronic device may in some cases take the form of any of the electronic watches or other wearable electronic devices described with reference to FIGS. 1-11, or other portable or wearable electronic devices. The electronic device 1200 can include a display 1212 (e.g., a light-emitting display), a processing unit 1202, a power source 1216, a memory 1204 or storage device, a sensor 1208, an input device 1206 (e.g., a crown), and an output device 1210 (e.g., a crown, a haptic device).

The processing unit 1202 can control some or all of the operations of the electronic device 1200. The processing unit 1202 can communicate, either directly or indirectly, with some or all of the components of the electronic device 1200. For example, a system bus or other communication mechanism 1218 can provide communication between the processing unit 1202, the power source 1216, the memory 1204, the sensor 1208, and the input device(s) 1206 and the output device(s) 1210.

The processing unit 1202 can be implemented as any electronic device capable of processing, receiving, or transmitting data or instructions. For example, the processing unit 1202 can be a microprocessor, a central processing unit (CPU), an application-specific integrated circuit (ASIC), a digital signal processor (DSP), or combinations of such devices. As described herein, the term "processing unit" is meant to encompass a single processor or processing unit, multiple processors, multiple processing units, or other suitably configured computing element or elements.

It should be noted that the components of the electronic device 1200 can be controlled by multiple processing units. For example, select components of the electronic device 1200 (e.g., a sensor 1208) may be controlled by a first processing unit and other components of the electronic device 1200 (e.g., the display 1212) may be controlled by a second processing unit, where the first and second processing units may or may not be in communication with each other. In some cases, the processing unit 1202 may determine a biological parameter of a user of the electronic device, such as an ECG for the user.

The power source 1216 can be implemented with any device capable of providing energy to the electronic device 1200. For example, the power source 1210 may be one or more batteries or rechargeable batteries. Additionally or alternatively, the power source 1210 can be a power connector or power cord that connects the electronic device 1200 to another power source, such as a wall outlet.

The memory 1204 can store electronic data that can be used by the electronic device 1200. For example, the memory 1204 can store electrical data or content such as, for example, audio and video files, documents and applications, device settings and user preferences, timing signals, control signals, and data structures or databases. The memory 1204 can be configured as any type of memory. By way of example only, the memory 1204 can be implemented as random access memory, read-only memory, Flash memory, removable memory, other types of storage elements, or combinations of such devices.

The electronic device 1200 may also include one or more sensors 1208 positioned almost anywhere on the electronic device 1200. The sensor(s) 1208 can be configured to sense one or more type of parameters, such as, but not limited to, pressure, light, touch, heat, movement, relative motion, biometric data (e.g., biological parameters), and so on. For example, the sensor(s) 1208 may include a heat sensor, a position sensor, a light or optical sensor, an accelerometer, a pressure transducer, a gyroscope, a magnetometer, a health monitoring sensor, and so on. Additionally, the one or more sensors 1208 can utilize any suitable sensing technology, including, but not limited to, capacitive, ultrasonic, resistive, optical, ultrasound, piezoelectric, and thermal sensing technology. In some examples, the sensors 1208 may include one or more of the electrodes described herein (e.g., one or more electrodes on an exterior surface of a cover that forms part of an enclosure for the electronic device 1200 and/or an electrode on a crown body, button, or other housing member of the electronic device 1200).

In various embodiments, the display 1212 provides a graphical output, for example associated with an operating system, user interface, and/or applications of the electronic device 1200. In one embodiment, the display 1212 includes one or more sensors and is configured as a touch-sensitive (e.g., single-touch, multi-touch) and/or force-sensitive display to receive inputs from a user. For example, the display 12012 may be integrated with a touch sensor (e.g., a capacitive touch sensor) and/or a force sensor to provide a touch- and/or force-sensitive display. The display 1212 is operably coupled to the processing unit 1202 of the electronic device 1200.

The display 1212 can be implemented with any suitable technology, including, but not limited to, liquid crystal display (LCD) technology, light emitting diode (LED) technology, organic light-emitting display (OLED) technology, organic electroluminescence (OEL) technology, or another type of display technology. In some cases, the display 1212 is positioned beneath and viewable through a cover that forms at least a portion of an enclosure of the electronic device 1200.

In various embodiments, the input devices 1206 may include any suitable components for detecting inputs. Examples of input devices 1206 include audio sensors (e.g., microphones), optical or visual sensors (e.g., cameras, visible light sensors, or invisible light sensors), proximity sensors, touch sensors, force sensors, mechanical devices (e.g., crowns, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 1206 may be configured to detect one or more particular types of input and provide a signal (e.g., an input signal) corresponding to the detected input. The signal may be provided, for example, to the processing unit 1202.

As discussed above, in some cases, the input device(s) 1206 include a touch sensor (e.g., a capacitive touch sensor) integrated with the display 1212 to provide a touch-sensitive display. Similarly, in some cases, the input device(s) 1206 include a force sensor (e.g., a capacitive force sensor) integrated with the display 1212 to provide a force-sensitive display.

In some cases, the input devices 1206 include a set of one or more electrodes. An electrode may be a conductive portion of the device 1200 that contacts or is configured to be in contact with a user. The electrodes may be disposed on one or more exterior surfaces of the device 1200, including a surface of an input device 1206 (e.g., a crown), a device enclosure, and the like. The processing unit 1202 may monitor for voltages or signals received on at least one of the electrodes. In some embodiments, one of the electrodes may be permanently or switchably coupled to a device ground. The electrodes may be used to provide an electrocardiogram (ECG) function for the device 1200. For example, a 2-lead ECG function may be provided when a user of the device 1200 contacts first and second electrodes that receive signals from the user. As another example, a 3-lead ECG function may be provided when a user of the device 1200 contacts first and second electrodes that receive signals from the user, and a third electrode that grounds the user to the device 1200. In both the 2-lead and 3-lead ECG embodiments, the user may press the first electrode against a first part of their body and press the second electrode against a second part of their body. The third electrode may be pressed against the first or second body part, depending on where it is located on the device 1200. In some cases, an enclosure of the device 1200 may function as an electrode. In some cases, input devices, such as buttons, crowns, and the like, may function as an electrode.

The output devices 1210 may include any suitable components for providing outputs. Examples of output devices 1210 include audio output devices (e.g., speakers), visual output devices (e.g., lights or displays), tactile output devices (e.g., haptic output devices), communication devices (e.g., wired or wireless communication devices), and so on, or some combination thereof. Each output device 1210 may be configured to receive one or more signals (e.g., an output signal provided by the processing unit 1202) and provide an output corresponding to the signal.

In some cases, input devices 1206 and output devices 1210 are implemented together as a single device. For example, an input/output device or port can transmit electronic signals via a communications network, such as a wireless and/or wired network connection. Examples of wireless and wired network connections include, but are not limited to, cellular, Wi-Fi, Bluetooth, IR, and Ethernet connections.

The processing unit 1202 may be operably coupled to the input devices 1206 and the output devices 1210. The processing unit 1202 may be adapted to exchange signals with the input devices 1206 and the output devices 1210. For example, the processing unit 1202 may receive an input signal from an input device 1206 that corresponds to an input detected by the input device 1206. The processing unit 1202 may interpret the received input signal to determine whether to provide and/or change one or more outputs in response to the input signal. The processing unit 1202 may then send an output signal to one or more of the output devices 1210, to provide and/or change outputs as appropriate.

As described above, one aspect of the present technology is the gathering and use of data available from various sources to provide haptic outputs, electrocardiograms, and the like. The present disclosure contemplates that, in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide electrocardiograms to the user and/or haptic outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence, different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of haptic feedback and electrocardiograms or other biometrics, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An electronic watch comprising:
an enclosure;
a touch-sensitive display positioned at least partially within the enclosure;
a processing unit operably coupled to the touch-sensitive display; and
a haptic device positioned at least partially within the enclosure and configured to provide a haptic output along an external surface of the enclosure, the haptic device comprising:
a contact member positioned to rotate around an axle;
an actuation member that is attached to a connection point of the contact member, wherein the actuation member is formed from a shape-memory alloy material and configured to contract in response to a signal generated by the processing unit, wherein a contraction of the actuation member rotates the contact member in a direction to produce at least a portion of the haptic output; and
a restoration mechanism configured to elongate the actuation member after the contraction of the actuation member.

2. The electronic watch of claim 1, wherein:
the actuation member is a first actuation member formed from a first shape-memory alloy material;
the signal is a first signal;
the restoration mechanism comprises a second actuation member formed from a second shape-memory alloy material; and
the second actuation member is configured to contract in response to a second signal generated by the processing unit.

3. The electronic watch of claim 2, wherein:
the direction is a first direction; and
contraction of the second actuation member in response to the second signal rotates the contact member in a second direction opposite the first direction.

4. The electronic watch of claim 3, wherein:
the first actuation member is coupled to a first spring via a first block member; and
the second actuation member is coupled to a second spring via a second block member.

5. The electronic watch of claim 4, wherein:
rotation of the contact member in the first direction compresses the second spring.

6. The electronic watch of claim 2, wherein:
the restoration mechanism comprises a spring; and
the spring and the second actuation member are coupled in series.

7. The electronic watch of claim 1, wherein:
a graphical output of the touch-sensitive display is visible along a front external surface; and
the haptic output is coordinated with a change in the graphical output.

8. The electronic watch of claim 1, wherein the axle is fixed with respect to the enclosure.

9. An electronic device comprising:
an enclosure;
a display positioned at least partially within the enclosure;
a contact member;
an actuation member comprising a shape-memory alloy and positioned within the enclosure, wherein the actuation member is attached to a connection portion of the contact member and is configured to change from a first shape to a second shape in response to an electrical signal;
a restoration mechanism configured to restore the actuation member from the second shape to the first shape; and
a processing unit operably coupled to the actuation member and configured to cause the electrical signal to be applied to the actuation member, wherein:
changing the actuation member from the first shape to the second shape rotates the contact member in a first direction to produce a first portion of a haptic output; and
restoring the actuation member from the second shape to the first shape rotates the contact member in a second direction opposite the first direction to produce a second portion of the haptic output.

10. The electronic device of claim 9, wherein:
the restoration mechanism comprises a torsion spring; wherein restoring the actuation member comprises exerting a torque on the contact member using the torsion spring.

11. The electronic device of claim 9, wherein:
the restoration mechanism comprises a first spring and a second spring.

12. The electronic device of claim 11, wherein:
the first spring is coupled to a first block member;
the second spring is coupled to a second block member; and
the actuation member contacts the first and second block members.

13. The electronic device of claim 12, wherein:
changing the actuation member from the first shape to the second shape compresses the first spring until a support member stops movement of the first block member.

14. The electronic device of claim 9, wherein:
the actuation member is a first actuation member;
the shape-memory alloy is a first shape-memory alloy; and
the restoration mechanism comprises a second actuation member formed from a second shape-memory alloy.

15. The electronic device of claim 14, wherein the restoration mechanism comprises a spring.

16. A method for producing a haptic output using an actuation member that is attached to a connection portion of a contact member and comprises a shape-memory alloy, the method comprising:
detecting an input at an electronic device using a processing unit of the electronic device;
in response to the input, producing an output signal;
in response to the output signal, applying an electrical current to the actuation member thereby causing the actuation member to contract, such that contraction of the actuation member rotates the contact member in a first direction to produce a first portion of the haptic output; and elongating the actuation member using a restoration mechanism, thereby rotating the contact member in a second direction opposite the first direction and producing a second portion of the haptic output.

17. The method of claim 16, wherein said elongating the actuation member of the electronic device comprises applying a torsional force to the actuation member using the restoration mechanism.

18. The method of claim 16, wherein:

the actuation member is a first actuation member;

the restoration mechanism comprises a second actuation member; and said elongating the actuation member using the restoration mechanism comprises contracting the second actuation member.

19. The method of claim 16, wherein:

said rotating the contact member in the first direction comprises rotating the contact member around an axle that is fixed with respect to a housing of the electronic device.

20. The method of claim 16, wherein:

the method further comprises displaying a graphical output using a touch-sensitive display; and said detecting the input comprises detecting a touch input along the touch-sensitive display.

\* \* \* \* \*